US010155797B2

(12) United States Patent
Zhang et al.

(10) Patent No.: US 10,155,797 B2
(45) Date of Patent: Dec. 18, 2018

(54) BINDING-INDUCED DNA NANOMACHINES

(71) Applicant: The Governors of the University of Alberta, Edmonton (CA)

(72) Inventors: Hongquan Zhang, Edmonton (CA); Xiaochun Le, Edmonton (CA); Xing-Fang Li, Edmonton (CA)

(73) Assignee: The Governors of the University of Alberta, Edmondon (CA)

( * ) Notice: Subject to any disclaimer, the term of this patent is extended or adjusted under 35 U.S.C. 154(b) by 276 days.

(21) Appl. No.: 15/262,737

(22) Filed: Sep. 12, 2016

(65) Prior Publication Data
US 2017/0073682 A1 Mar. 16, 2017

Related U.S. Application Data

(60) Provisional application No. 62/217,338, filed on Sep. 11, 2015.

(51) Int. Cl.
| | |
|---|---|
| *C12N 15/115* | (2010.01) |
| *C07K 14/47* | (2006.01) |
| *C07K 14/49* | (2006.01) |
| *C12N 9/22* | (2006.01) |
| *C12N 15/11* | (2006.01) |
| *A61K 38/00* | (2006.01) |

(52) U.S. Cl.
CPC .............. *C07K 14/49* (2013.01); *C07K 14/47* (2013.01); *C12N 9/22* (2013.01); *C12N 15/111* (2013.01); *C12N 15/115* (2013.01); *A61K 38/00* (2013.01); *C12N 2310/16* (2013.01); *C12N 2320/32* (2013.01)

(58) Field of Classification Search
CPC .................................. C07K 14/49; C12N 9/22
See application file for complete search history.

(56) References Cited

PUBLICATIONS

Amir et al., "Universal Computing by DNA Origami Robots in a Living Animal," Nature Nanotechnology, May 2014, vol. 9 (5), pp. 353-357.
Bath et al., "DNA Nanomachines," Nature Nanotechnology, May 2007, vol. 2 (5), pp. 275-284.
Bhatt et al., "Dissociation and Degradation of Thiol-modified DNA on Gold Nanoparticles in Aqueous and Organic Solvents," Langmuir, May 2007, vol. 27 (10), pp. 6132-6137.
Sha et al., "A Synthetic DNA Motor That Transports Nanoparticles Along Carbon Nanotubes," Nature Nanotechnology, Jan. 2014, vol. 9 (1), pp. 39-43.
Deng et al., "Assembly of Multiple DNA Components through Target Binding toward Homogeneous, Isothermally Amplified, and Specific Detection of Proteins," Analytical Chemistry, Jun. 2014, vol. 86 (4), pp. 7009-7016.
Douglas et al., "A Logic-Gated Nanorobot for Targeted Transport of Molecular Payloads," Science, Feb. 2012, vol. 335 (6070), pp. 831-834.
Dubertret et al., "Single-Mismatch Detection Using Gold-Quenched Fluorescent Oligonucleotides," Nature Biotechnology, Apr. 2001, vol. 19 (4), pp. 365-370.
Elghanian et al., "Selective Colorimetric Detection of Polynucleotides Based on the Distance-Dependent Optical Properties of Gold Nanoparticles," Science, Aug. 1997, vol. 277 (5329), pp. 1078-1081.
Huang et al., "Aptamer-Modified Gold Nanoparticles for Colorimetric Determination of Platelet-Derived Growth Factors and Their Receptors," Analytical Chemistry, Sep. 2005, vol. 77 (17), pp. 5735-5741.
Hurst et al., "Maximizing DNA Loading on a Range of Gold Nanoparticle Sizes," Analytical Chemistry, Dec. 2006, vol. 78 (24), pp. 8313-8318.
Karagiannis et al., "Molecular Machines Like Myosin Use Randomness to Behave Predictably," Chemical Reviews, Jan. 2014, vol. 114 (6), pp. 3318-3334.
Li et al., "A Multicolor Nanoprobe for Detection and Imaging of Tumor-Related mRNAs in Living Cells," Angewandte Communications, Jul. 2012, vol. 51 (30), pp. 7426-7430.
Liber et al., "A Bipedal DNA Motor that Travels Back and Forth between Two DNA Origami Tiles," Small, Feb. 2015, vol. 11 (5), pp. 568-575.
Liu et al., "A DNA Tweezer-Actuated Enzyme Nanoreactor," Nature Communications, Jul. 2013, vol. 4, pp. 1-5.
Liu et al., "DNA Nanomachines and Their Functional Evolution," Chemical Communications, Apr. 2009, vol. 19, pp. 2625-2636.
Lund et al., "Molecular Robots Guided by Prescriptive Landscapes," Nature, May 2010, vol. 465 (7295), pp. 206-210.
Muscat et al., "Small Molecule Signals that Direct the Route of a Molecular Cargo," Small, Dec. 2012, vol. 8 (23), pp. 3593-3597.
Pan et al., "Recent Progress on DNA Based Walkers," Current Opinion in Biotechnology, Aug. 2015, vol. 34, pp. 56-64.
Rajendran et al., "Direct and Real-Time Observation of Rotary Movement of a DNA Nanomechanical Device," Journal of the American Chemical Society, Jan. 2013, vol. 135 (3), pp. 1117-1123.
Seferos et al., "Polyvalent DNA Nanoparticle Conjugates Stabilize Nucleic Acids," Nano Letters, Jan. 2009, vol. 9 (1), pp. 308-311.

(Continued)

*Primary Examiner* — Scott Long
(74) *Attorney, Agent, or Firm* — Borden Ladner Gervais LLP

(57) ABSTRACT

The invention provides a binding-induced DNA nanomachine that can be activated by proteins and nucleic acids. This new type of nanomachine harnesses specific target binding to trigger assembly of separate DNA components that are otherwise unable to spontaneously assemble. Three-dimensional DNA tracks of high density are constructed on gold nanoparticles functionalized with hundreds of single-stranded oligonucleotides and tens of an affinity ligand. A DNA swing arm, free in solution, can be linked to a second affinity ligand. Binding of a target molecule to the two ligands brings the swing arm to AuNP and initiates autonomous, stepwise movement of the swing arm around the AuNP surface. The movement of the swing arm generates hundreds of oligonucleotides in response to a single binding event. The new nanomachines have several unique and advantageous features over DNA nanomachines that rely on DNA self-assembly.

19 Claims, 20 Drawing Sheets

Specification includes a Sequence Listing.

(56) References Cited

PUBLICATIONS

Song et al., "Smart Nanomachines Based on DNA Self-Assembly," Small, Jul. 2013, vol. 9 (14), pp. 2382-2392.

Storhoff et al., "Sequence-Dependent Stability of DNA-Modified Gold Nanoparticles," American Chemical Society, Jul. 2002, vol. 18, pp. 6666-6670.

Suda et al., "Base-Dependent Competitive Adsorption of Single-Stranded DNA on Gold," Journal of the American Chemical Society, Jul. 2003, vol. 125 (30), pp. 9014-9015.

Thomas et al., "A Mechano-Electronic DNA Switch," Journal of the American Chemical Society, Jul. 2012, vol. 134, pp. 13738-13748.

Tian et al., "A DNAzyme That Walks Processively and Autonomously along a One-Dimensional Track," Angewandte Chemie (International ed. in English), Jul. 2005, vol. 44 (28), pp. 4355-4358.

Uddayasankar et al., "Analytical Performance of Molecular Beacons on Surface Immobilized Gold Nanoparticles of Varying Size and Density," Analytica Chimica Acta, Nov. 2013, vol. 803, pp. 113-122.

Venkataraman et al., "An Autonomous Polymerization Motor Powered by DNA Hybridization," Nature Nanotechnology, Aug. 2007, vol. 2 (8), pp. 490-494.

Wang et al., "DNA Machines: Bipedal Walker and Stepper," Nano Letters, Jan. 2011, vol. 11 (1), pp. 304-309.

Wang et al., "DNA Switches: From Principles to Applications," Angewandte Chemie (International ed.), Jan. 2015, vol. 54 (4), pp. 1098-1129.

Wickham et al., "Direct Observation of Stepwise Movement of a Synthetic Molecular Transporter," Nature Nanotechnology, Mar. 2011, vol. 6, pp. 166-169.

Wu et al., "A DNAzyme-Gold Nanoparticle Probe for Uranyl Ion in Living Cells," Journal of the American Chemical Society, Mar. 2013, vol. 135 (14), pp. 5254-5257.

Yang et al., "An Electrochemically Actuated Reversible DNA Switch," Nano Letters, Apr. 2010, vol. 10 (4), pp. 1393-1397.

Yin et al., "A Unidirectional DNAWalker That Moves Autonomously along a Track," Angewandte Chemie (International ed.), Sep. 2004, vol. 43 (37), pp. 4906-4911.

Yurke et al., "A DNA-Fuelled Molecular Machine Made of DNA," Nature, Aug. 2000, vol. 406, pp. 605-608.

Zhang et al., "Assembling DNA through Affinity Binding to Achieve Ultrasensitive Protein Detection," Angewandte Chemie (International ed.), Oct. 2013, vol. 52 (41), pp. 10698-10705.

Zhang et al., "Binding-Induced DNA Assembly and Its Application to Yoctomole Detection of Proteins," Analytical Chemistry, Jan. 2012, vol. 84 (2), pp. 877-884.

Zhou et al., "Reversible Regulation of Protein Binding Affinity by a DNA Machine," Journal of the American Chemical Society, Jan. 5, 2012, vol. 134 (3), pp. 1416-1418.

Zwanikken et al., "Local Ionic Environment around Polyvalent Nucleic Acid-Functionalized Nanoparticles," The Journal of Physical Chemistry C, Jul. 24, 2011, vol. 115 (33), pp. 16368-16373.

FIG. 1A
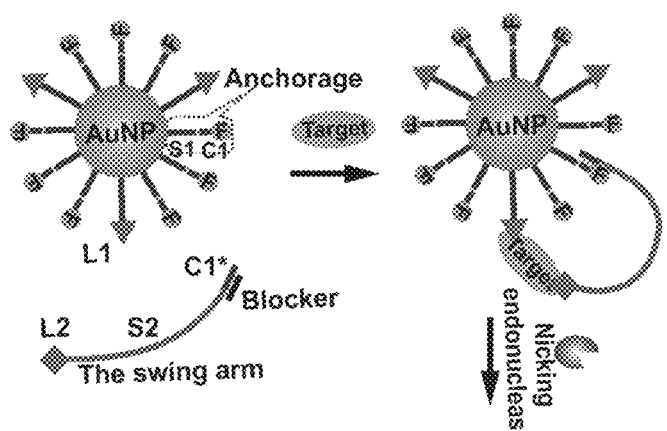
FIG. 1B
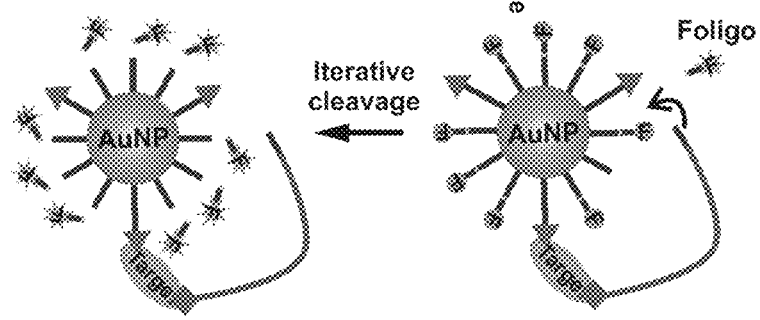
FIG. 1C

FIG. 18A
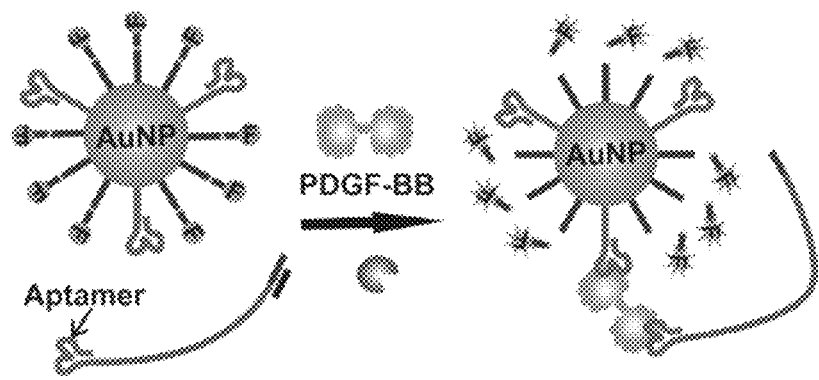
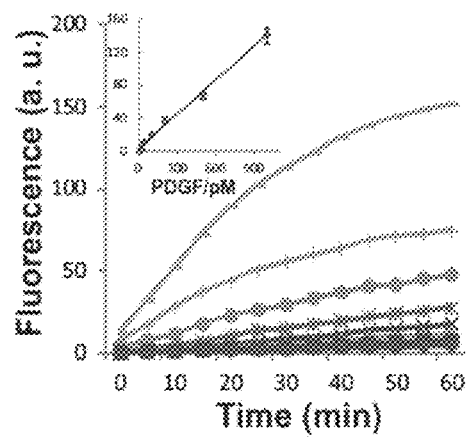
FIG. 18B
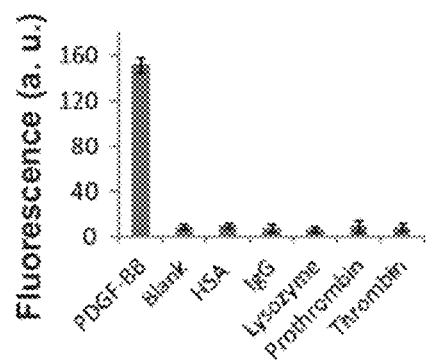
FIG. 18C

FIG. 20A
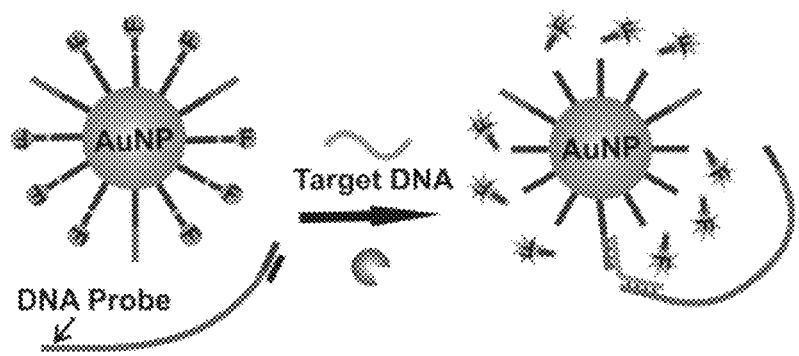
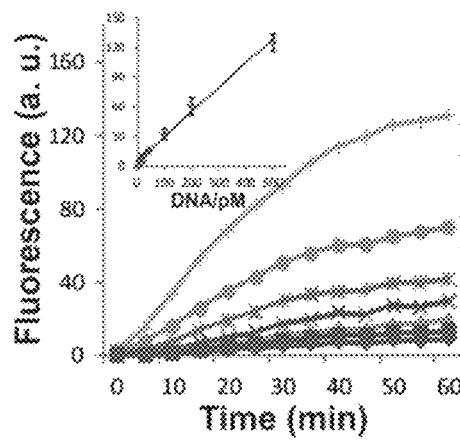
FIG. 20B
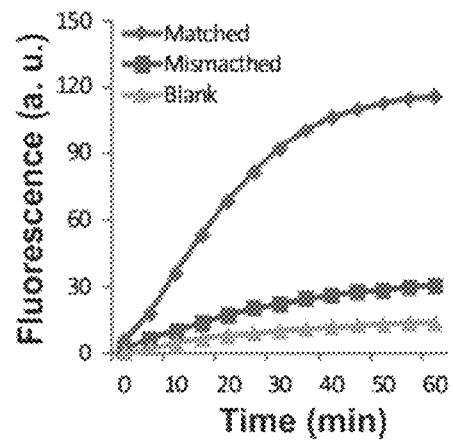
FIG. 20C

BINDING-INDUCED DNA NANOMACHINES

RELATED APPLICATION

This application claims the benefit of priority of U.S. Provisional Patent Application No. 62/217,338, filed Sep. 11, 2015, which are hereby incorporated by reference.

BACKGROUND

Biological or synthetic molecular machines, assembled with molecular components, perform quasi-mechanical movements in response to specific external stimuli.[1] The exquisite specificity, predictability, and diversity of DNA hybridization have inspired the use of DNA to construct various nanomachines, including DNA walkers,[2] DNA tweezers,[3] DNA motors,[4] DNA robots,[5] and DNA switch[6]. These DNA nanomachines are constructed on the basis of DNA self-assembly,[7] usually activated by nucleic acids. The few non-nucleic acid nanomachines require conformation changes of the functional DNA upon molecular interactions.[8] There are very few protein-activated nanomachines.[9] Accordingly, there is a need for a new nanomachines, for example, that can be activated by proteins and nucleic acids.

SUMMARY

The invention provides a nanomachine comprising:
a nanoparticle;
a first polynucleotide, the first polynucleotide having a first short sequence and a first spacer sequence, the first spacer sequence being conjugated to the nanoparticle and the first short sequence being conjugated to a first ligand;
a second polynucleotide, having a first end and a second end, the first end being conjugated to the nanoparticle and the second end being conjugated to a second ligand;
a third polynucleotide having a second short sequence, a second spacer sequence and a third ligand, the third ligand being conjugated to the second spacer sequence, the second short sequence being complementary to at least a portion of the first short sequence of the first polynucleotide;
a fourth polynucleotide that is complimentary to at least a portion of the second short sequence and the second spacer sequence of the third polynudeotide and being bound to the third polynucleotide; and
a target molecule that binds to the second ligand and the third ligand where, upon binding, the third polynucleotide is brought into proximity of the first polynudeotide such that the fourth polynucleotide is displaced and the first short sequence binds to the complimentary second short sequence, producing an enzymatic cleavage site, which is then cleaved by an enzyme and releasing the first ligand.

The nanoparticle can be a gold nanoparticle.
The enzymatic cleavage site can be a nicking endonuclease site.
The target molecule can be a protein or nucleic acid.
The protein can be streptavidin. The protein can also be platelet derived growth factor.
The second and third ligands can be biotin. The second and third ligands can be aptamers configured to bind to platelet derived growth factor.
The second and third ligands, and the target molecule can comprise a nucleic acid wherein the second and third ligands are complimentary to at least a portion of the target molecule.

The first ligand can be an effector molecule. The effector molecule can be a labeling molecule, an affinity tag, a chemotherapeutic, a cytotoxic agent, an active peptide, a contrast agent, a radiolabel, DNA, or a small molecule inhibitor.

The invention also provides a method for effector molecule delivery comprising:
providing a functionalized nanoparticle having a first polynucleotide, the first polynucleotide having a first short sequence and a first spacer sequence, the first spacer sequence being conjugated to the nanoparticle and the first short sequence being conjugated to a first ligand; a second polynucleotide, having a first end and a second end, the first end being conjugated to the nanopartide and the second end being conjugated to a second ligand; a third polynucleotide having a second short sequence, a second spacer sequence and a third ligand, the third ligand being conjugated to the second spacer sequence, the second short sequence being complementary to at least a portion of the first short sequence of the first polynucleotide; and a fourth polynucleotide that is complimentary to at least a portion of the second short sequence and the second spacer sequence of the third polynucleotide and being bound to the third polynucleotide;
adding a target molecule to the functionalized nanoparticle such that the target molecule binds to the second and third ligands, thereby bringing the third polynucleotide into proximity of the first polynucleotide such that the fourth polynucleotide is displaced and the first short sequence binds to the complimentary second short sequence, producing an enzymatic cleavage site;
enzymatically cleaving the first and third polynucleotides at the enzymatic cleavage site; and
releasing the first ligand, wherein the first ligand is the effector molecule.

The nanoparticle can be a gold nanoparticle.
The enzymatic cleavage site can be a nicking endonuclease site.
The target molecule can be a protein or nucleic acid. The protein can be streptavidin and the second and third ligands can be biotin.
The protein can be platelet derived growth factor and the second and third ligands can be aptamers configured to bind to platelet derived growth factor.
The second and third ligands, and the target molecule can comprise a nucleic acid wherein the second and third ligands are complimentary to at least a portion of the target molecule.
The effector molecule can be a labeling molecule, an affinity tag, a chemotherapeutic, a cytotoxic agent, an active peptide, a contrast agent, a radiolabel, DNA, or a small molecule inhibitor.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 1 A, B, C_depicts a binding-induced DNA nanomachine. FIG. 1A depicts binding to a target brings the swing arm onto the AuNP surface, inducing the hybridization between C1' on the swing arm and C1 on the anchoragem. FIG. 1B the C1*:C1 hybrid has a nicking endonuclease recognition site. The nicking endonuclease cleaves C1 from the hybrid, leaving single-stranded C1* available. The swing arm moves along the AuNP surface, bringing C1* to hybridize with C1 on the next anchorage. FIG. 1C The iterative operation continues: movement of the swing arm along the AuNP surface, formation of the C1':C1 hybrid, and enzymatic cleavage of C1 from the hybrid. The cleaved oligonucleotide is fluorescent (Foligo) and is detected for monitoring the nanomachine operation. The entire event is initiated by binding of a single target molecule to the two ligands (L1 and L2).

FIG. 12 A, B, shows modulation of the nanomachine to generate Foligos upon a single binding event. The modulation was achieved by altering the loading amount of anchorage on each AuNP.

FIG. 13 A, B, show reduction of the initial rate of the nanomachine by increasing the blocker length.

FIG. 14 A, B, shows reduction of the initial rate of the nanomachine by reducing the thymine content of S1 on the anchorage.

FIG. 17 A, B, C are graphs depicting the initial rate is proportional to the concentration of streptavidin.

FIG. 18A depicts schematic of the nanomachine responsive to PDGF-BB. FIG. 18B Progress curves of the nanomachine in response to various concentrations of PDGF-BB. Inset: concentration-dependent fluorescence. FIG. 18C Specific response of the nanomachine to the target molecule.

FIG. 19 A, B, are graphs depicting the specific response of the nanomachine to PDGF-BB spiked in cell lysate.

FIG. 20A depicts Schematic of the nanomachine responsive to the Smallpox gene. FIG. 20B Progress curves of the nanomachine in response to various concentrations of the Smallpox gene. Inset: concentration-dependent fluorescence. FIG. 20(c) Differentiation of the fully matched target from a single-mismatch.

DETAILED DESCRIPTION

Figure 2:
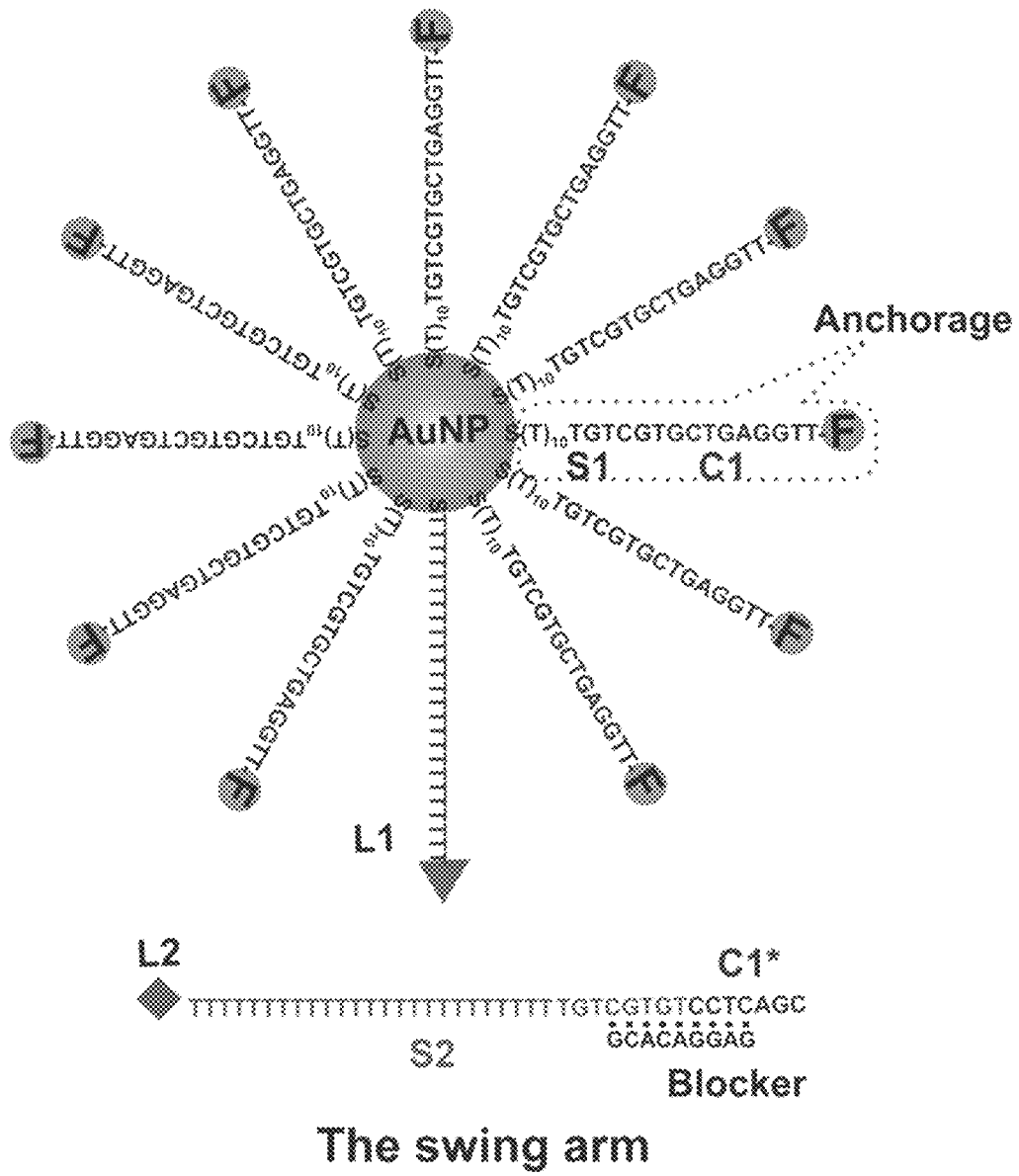
FIG. 2 depicts a design of the binding-induced DNA nanomachine.

The invention provides a binding-induced DNA nanomachine that can be activated by proteins and nucleic acids. This new type of nanomachine harnesses specific target binding to trigger assembly of separate DNA components that are otherwise unable to spontaneously assemble. Three-dimensional DNA tracks of high density are constructed on gold nanoparticles functionalized with hundreds of single-stranded oligonucleotides and tens of an affinity ligand. A DNA swing arm, free in solution, is linked to a second affinity ligand. Binding of a target molecule to the two ligands brings the swing arm to AuNP and initiates autonomous, stepwise movement of the swing arm around the AuNP surface. The movement of the swing arm generates hundreds of oligonucleotides in response to a single binding event. We demonstrate three nanomachines that are specifically activated by streptavidin, platelet-derived growth factor, and the Smallpox gene. Substituting the ligands enables the nanomachine to respond to other molecules. The new nanomachines have several unique and advantageous features over DNA nanomachines that rely on DNA self-assembly.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Con-*

*densed Chemical Dictionary* 14*th* Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Binding-Induced DNA Nanomachines Triggered by Proteins and Nucleic Acids.

We report here a new type of DNA nanomachine that is activated by protein binding. Distinct from existing DNA nanomachines that are formed by DNA self-assembly, the new nanomachine is constructed with and activated by binding-induced DNA assembly.[10] The binding of a single target molecule with two ligand molecules triggers the assembly of separate DNA components that are otherwise unable to spontaneously assemble. Taking advantage of the high DNA loading capacity of gold nanoparticles (AuNPs), we constructed a binding-induced nanomachine to possess high density, three-dimensional DNA tracks, representing an advance over the existing one- or two-dimensional DNA nanomachines. Specific target binding triggers autonomous, stepwise movement of a swing arm along the AuNP surface, generating hundreds of oligonucleotides in response to a single binding event. The nanomachine is applicable to any molecules capable of binding simultaneously to two ligands.

We designed the binding-induced DNA nanomachine to consist of a DNA-functionalized AuNP and a swing arm (FIG. 1, FIG. 2, in the Example below). Onto the surface of a single AuNP are conjugated hundreds of single-stranded anchorages and tens of an affinity ligand L1 (Determination of anchorage loading on AuNPs is described in the Example below). Each anchorage is composed of a short sequence C1 that is attached onto the AuNP via a DNA spacer S1. On the free end of C1, we conjugated a fluorescent tag (FAM), to enable real-time monitoring of the nanomachine operation. Fluorescence is quenched because of the extremely high efficiency of fluorescence quenching by AuNPs.[11] The swing arm is composed of a sequence C1* complementary to C1, and a poly thymine spacer S2 serving as a flexible linker between C1* and a second ligand L2. Varying the number of thymines (S2) enables us to create a desired arm length between C1* and L2 (Table 1 in the Example below).

FIG. 1 depicts a binding-induced DNA nanomachine. (a) Binding to a target brings the swing arm onto the AuNP surface, inducing the hybridization between C1* on the swing arm and C1 on the anchorage. (b) The C1*:C1 hybrid has a nicking endonuclease recognition site. The nicking endonuclease cleaves C1 from the hybrid, leaving single-stranded C1* available. The swing arm moves along the AuNP surface, bringing C1* to hybridize with C1 on the next anchorage. (c) The iterative operation continues: movement of the swing arm along the AuNP surface, formation of the C1*:C1 hybrid, and enzymatic cleavage of C1 from the hybrid. The cleaved oligonucleotide is fluorescent (Foligo) and is detected for monitoring the nanomachine operation. The entire event is initiated by binding of a single target molecule to the two ligands (L1 and L2).

Figure 3:
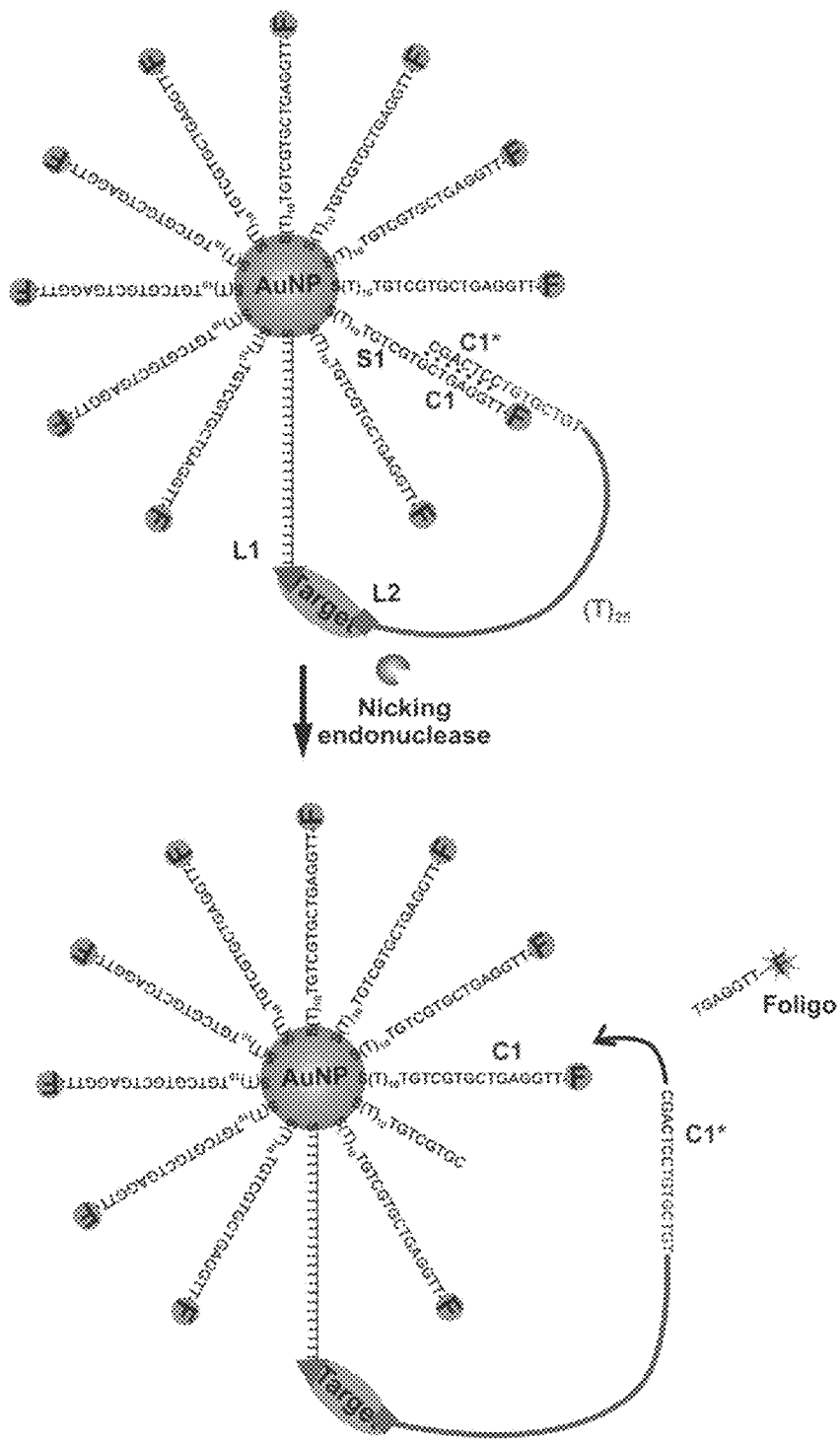
FIG. 3 depicts the operation of the binding-induced DNA nanomachine.

We designed C1 and C1* to contain only 7 complementary nucleotides so that their hybrid is unstable at ambient temperature. We also designed a DNA blocker, complementary to one segment of C1* and another segment of S2, to further minimize any target-independent spontaneous hybridization between C1 and C1* (FIG. 2). Therefore, when there is no interaction between the swing arm and the AuNP, the nanomachine is inactive. However, binding of the target molecule (e.g., a protein) to both ligands L1 and L2 activates the operation of the nanomachine in the following manner. The binding of L1 and L2 to the same target molecule places the swing arm onto the AuNP surface. Consequently, the complementary sequences C1 and C1* are brought into close proximity, allowing for intramolecular binding-induced assembly. The intramolecular interaction dramatically increases the local effective concentrations of C1 and C1*, enabling the C1:C1* hybrid to have a higher stability than that of the hybrid between the blocker and the swing arm, and driving the formation of a stable hybrid between C1 and C1* by displacing the blocker from the swing arm. The hybridization forms a complete recognition sequence of a nicking endonuclease (NEase) (FIG. 3). The NEase-catalyzed cleavage of C1 from the C1*:C1 hybrid liberates C1*, making it available for hybridization with another C1 on the same AuNP. Thus, the enzymatic cleavage drives the swing arm to move autonomously along the AuNP surface until all cleavages are complete and the nanomachine stops.

The NEase-catalyzed cleavage of C1 releases the fluorescently-labeled oligonucleotide (Foligo) from the AuNP. The free Foligos in solution are not quenched by AuNP and become fluorescent. As the swing arm moves around the AuNP and cleaves off C1, the nanomachine generates increasing fluorescence. Therefore, we are able to monitor the nanomachine operation in real-time by detecting the fluorescence of the released Foligos.

In principle, altering the ligand molecules enables the nanomachine to be specifically responsive to any target molecules (e.g., proteins and nucleic acids) that can be bound simultaneously by two ligand molecules. We describe here three examples of nanomachines that are activated by biotin binding to streptavidin, aptamer binding to platelet-derived growth factor (PDGF), and hybridization to Smallpox gene.

Figure 4A:
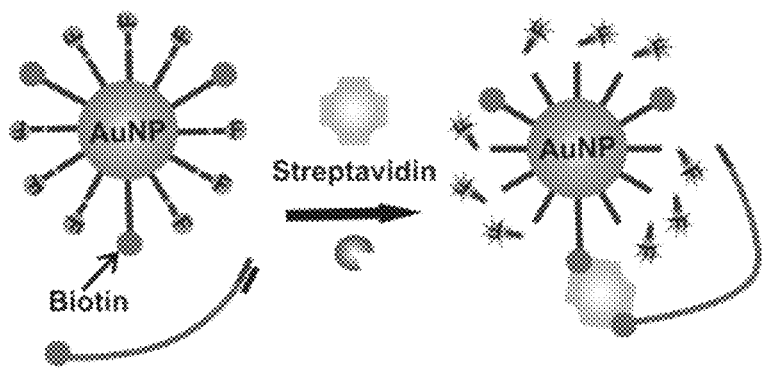
FIG. 4A depicts binding of streptavidin to two biotin molecules brings the swing arm to AuNP and leads to enzymatic cleavage of anchorage from AuNP.
Figure 4B:
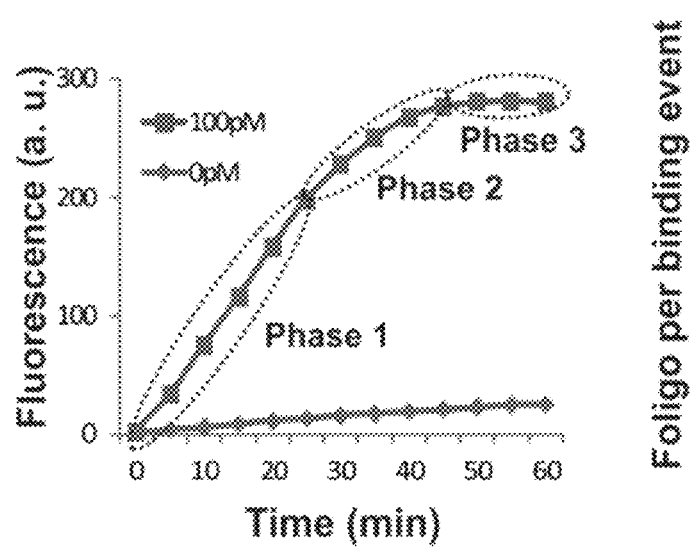
FIG. 4B Typical progress curve indicating three phases of the nanomachine operation.

To test the feasibility, we first constructed a DNA nanomachine that is triggered by binding of two biotin molecules to a streptavidin molecule. One biotin molecule, serving as ligand L1, is attached to the AuNP. The second biotin, serving as ligand L2, is conjugated to the swing arm (FIG. 4A). In the absence of streptavidin, the swing arm and the AuNP exist separately in the solution, and the nanomachine is non-operational. Upon the addition of 100 pM streptavidin to the solution, binding of streptavidin to two biotin molecules (L1 and L2) brings the swing arm into close proximity with the anchorage on the AuNP, activating the nanomachine. Enzymatic cleavage of anchorage from AuNPs gives rise to fluorescence (FIG. 4B). The progress curve reveals that the nanomachine operates in three phases. Once activated, the nanomachine generates Foligo at an initial linear rate for about 25 min (phase 1). The streptavidin binding places the swing arm in close proximity to anchorages on the AuNP. The enzymatic cleavage follows steady-state kinetics. After a large fraction of anchorages is cleaved off from the AuNP, fewer anchorages with C1 are available for hybridization to C1*. The nanomachine operation becomes slower (phase 2). Finally, when no C1 on anchorages is accessible by the swing arm, the operation of nanomachine completes and the fluorescence plateaus (phase 3).

Figure 5A:
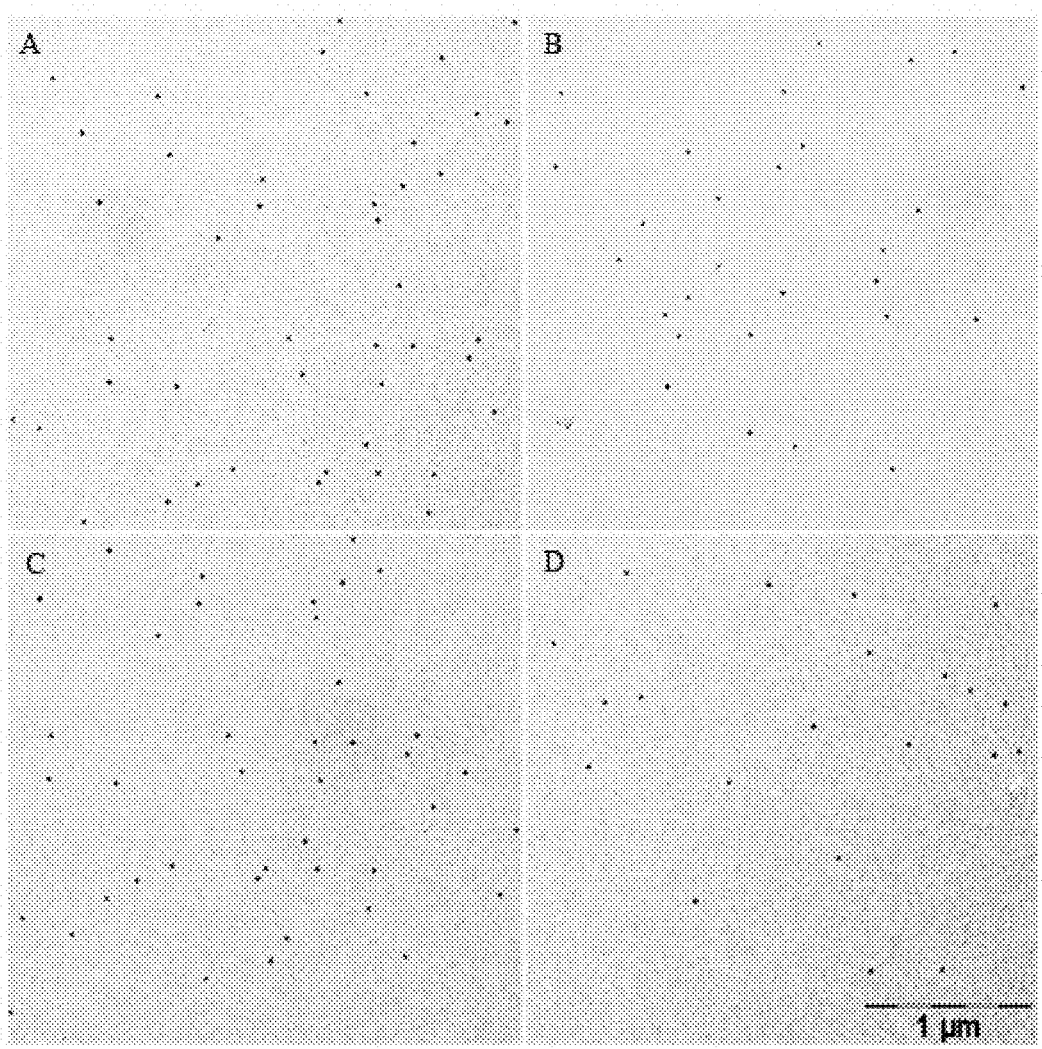
FIG. 5A depicts TEM images of nanomachine solutions containing 0.2 nM DNA-functionalized AuNP, 4 nM biotin-labeled swing arm, and 0 (A), 25 (B), 60 (C) or 100 (D) pM streptavidin, and FIG. 5B UV-visible absorption spectra of nanomachine solutions containing 0.2 nM DNA-functionalized AuNP, 4 nM biotin-labeled swing arm, and 0, 25, 60, or 100 pM streptavidin.
Figure 5B:
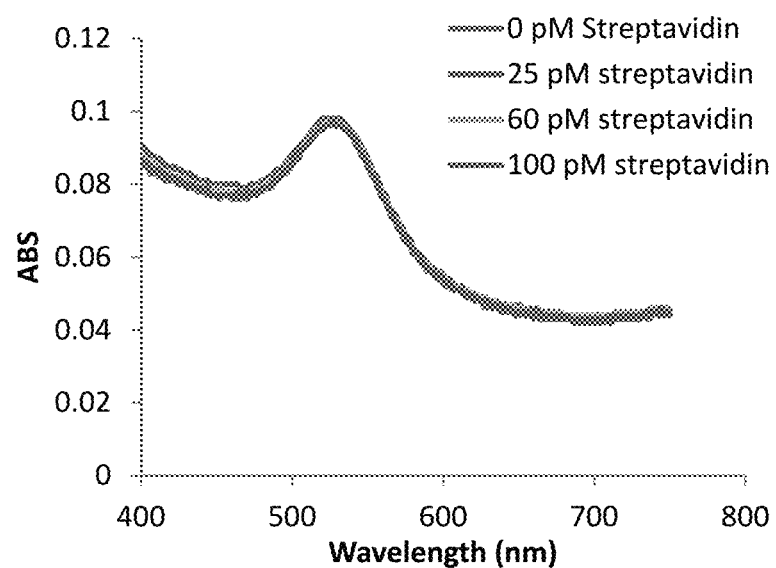

We then tested the efficiency of the nanomachine by monitoring the number of the NEase-cleaved Foligos, originating from a single streptavidin binding, and the subsequent operation of the nanomachine. To ensure that only a single streptavidin molecule is available to bind onto an AuNP, we used a limiting amount of streptavidin and an excess of AuNP. We prepared three solutions containing 200 pM AuNP and 100 pM, 60 pM, or 25 pM streptavidin. Thus, in all three cases, only a single streptavidin molecule could be present on each activated nanomachine. This is supported by TEM and UV-Vis analyses, showing no AuNP aggregation (FIGS. 5A and 5B). The progress curves (FIG. 6) show the time-dependent increases of the overall fluorescence intensity. These results are expected from the operation of the nanomachines. The overall fluorescence intensity is proportional to the total concentration of streptavidin (25, 60, and 100 pM) because a higher concentration of streptavidin in the solution activates more nanomachines, and therefore cleaves off more Foligos. We have determined the number of Foligos generated from a single nanomachine (activated by a single binding event). FIG. 7 shows that the number of Foligos cleaved off from each nanomachine follows a similar profile. These results suggest that individual nanomachines operate similarly in response to a single binding event. This is understandable because under the conditions of limiting streptavidin concentration, each streptavidin molecule activates a nanomachine by uniting the swing arm and the AuNP, and each activated nanomachine operates independently. FIG. 7 shows that each nanomachine converts a single streptavidin binding event into the cleavage of ~375 Foligos from a single AuNP. We used 20 nm AuNP and conjugated an average of ~410 anchorages (containing Foligos) onto each AuNP. These results indicate that ~91% of the total Foligos on the AuNP were cleaved off in response to a single binding event, suggesting that our nanomachine is highly efficient.

We compared the performances of three nanomachines that were constructed to have varying lengths of swing arms (40, 60, or 80 n.t.). Similar progress curves from the operation of these three nanomachines (FIG. 8) indicate that these swing arms provide sufficient spatial distance to reach most anchorages on the AuNP. Estimations of the overall size of the loop after the binding-induced formation of the C1*:C1 hybrid support these results (FIG. 3).

Figure 10:
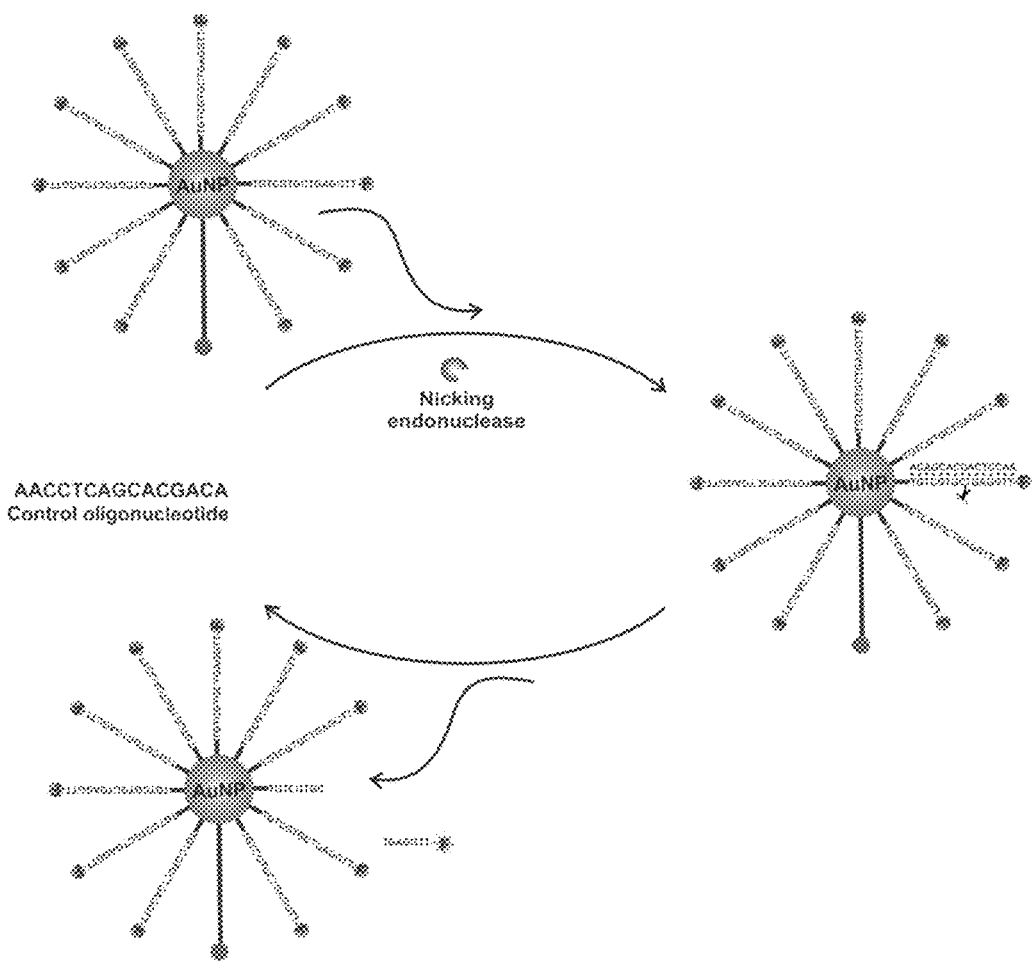
FIG. 10 depicts hybridization by a control oligonucleotide containing 15 complementary bases and the subsequent endonuclease cleavage of the anchorage.
Figure 11:
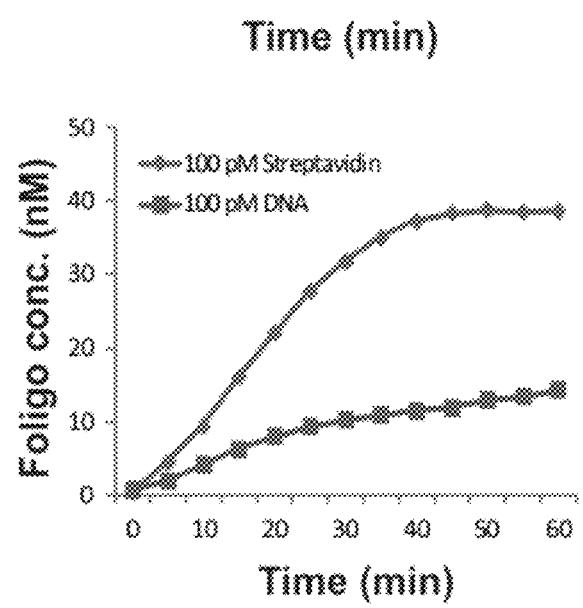
FIG. 11 Comparison of anchorage cleavage induced by 100 pM streptavidin and 100 pM control oligonucleotide.

We reasoned that the enzymatic cleavage within the nanomachine occurs at a fast rate because of the binding-induced formation of intramolecular hybridization between C1* and C1. To prove it, we compared the anchorage cleavage from the nanomachine that is triggered by 100 pM streptavidin (FIG. 9) with the anchorage cleavage from the spontaneous hybridization to 100 pM control oligonucleotide (FIG. 10). The initial rate of streptavidin-induced nanomachine cleavage is 1.11 $nM^{-1}$ $min^{-1}$, which is significantly larger than that (0.38 $nM^{-1}$ $min^{-1}$) of the DNA-induced cleavage (FIG. 11). The higher cleavage rate enables the nanomachine operation to be completed within a short time. Additionally, in response to a single streptavidin binding, each active nanomachine entity operates with a similar initial rate that is independent of streptavidin concentration (FIG. 7).

Figure 12A:
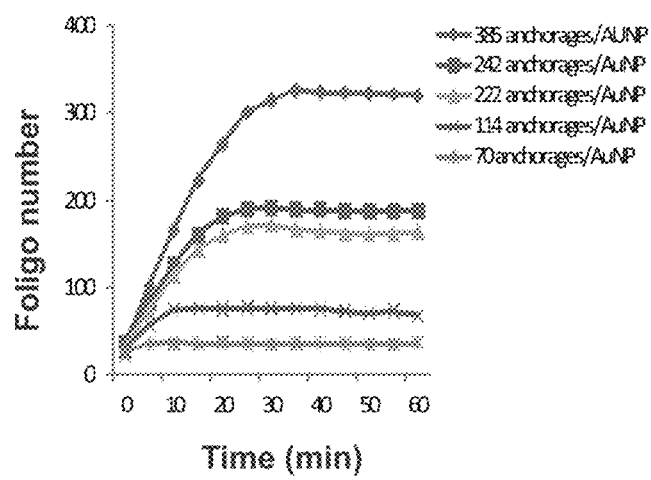
FIG. 12A The number of Foligos cleaved off from the different nanomachines. The five nanomachines contained different numbers of anchorages on each AuNP (from 70 to 385 anchorages per AuNP).
Figure 12B:
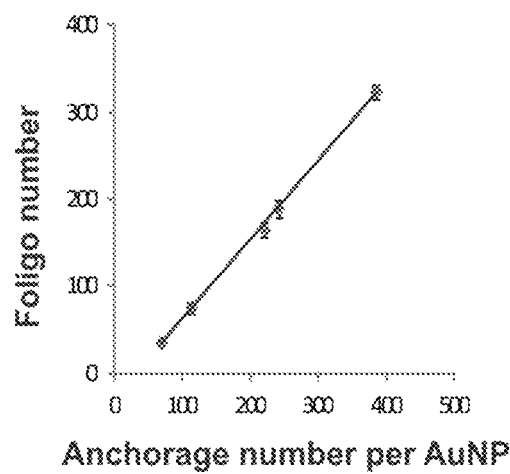
FIG. 12B The number of Foligos generated from a single binding event is proportional to the loading amount of anchorage per AuNP. Each solution contained 200 pM AuNP and 100 pM streptavidin.
Figure 13A:
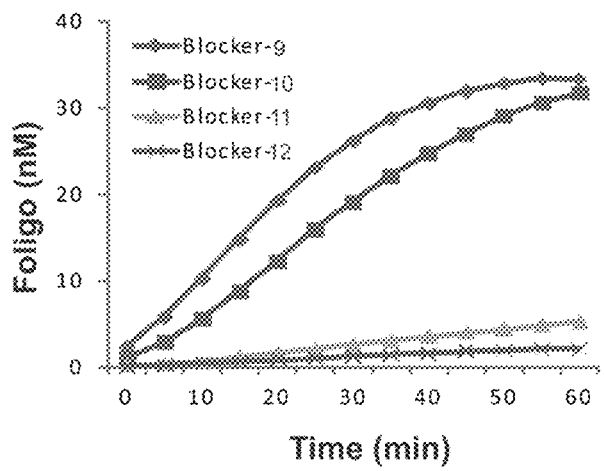
FIG. 13A Generation of Foligo from nanomachines containing blockers of varying lengths (9, 10, 11 or 12 nt).
Figure 13B:
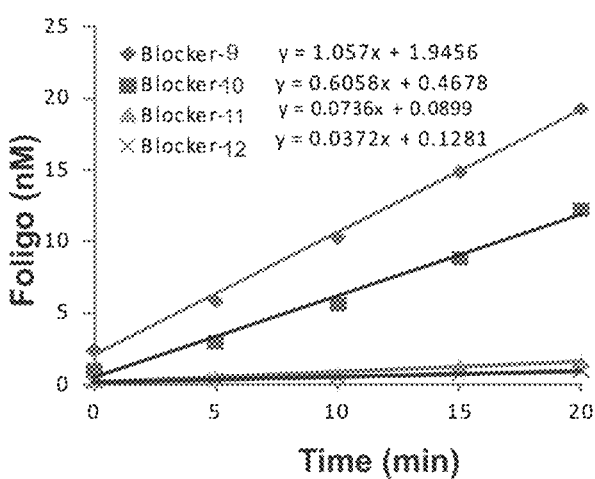
FIG. 13B Calculation of the initial rates using data of the first 20 min. The increase in blocker length reduces the initial rate of the nanomachine. The sequences of blockers are listed in Table 1, and 100 nM of each blocker was used.
Figure 14A:
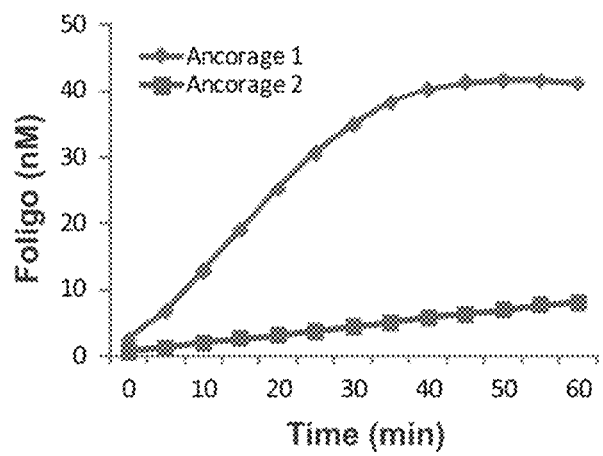
FIG. 14A Foligo generation curves using two anchorages with different S1 sequences.

The nanomachine can be modulated by varying several parameters. We observed that the number of Foligos generated from a single binding event is proportional to the number of anchorages loaded onto each AuNP (FIGS. 12A and 12B). Thus, altering the anchorage loading amount can manipulate the nanomachine to release desirable oligonucleotides in response to a single molecule binding. In addition, we are able to use blockers to reduce target-independent hybridization between C1 and C1* and to tune the initial rate of the nanomachine. The increase of blocker length reduces the initial rate (FIGS. 13A and 13B). Because nucleotides have varying binding affinity to the AuNP surface (A>C≥G>T),[11] varying the spacer S1 sequence can alter the interaction of the anchorage with AuNP, thereby impacting hybridization of C1* with C1 and the initial rate of the operation (FIG. 14A, B).

Figure 15:
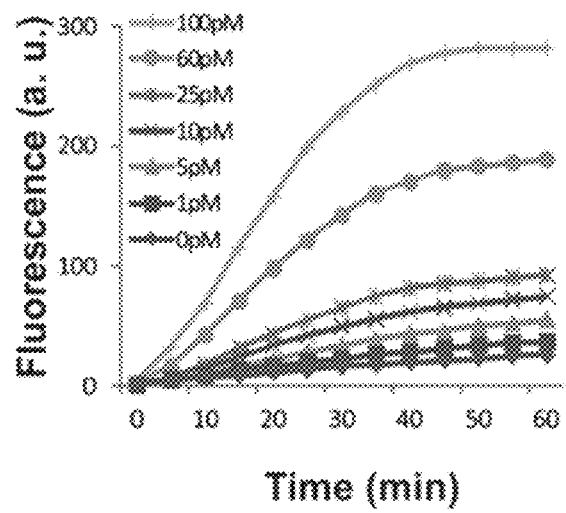
FIG. 15 depicts the response of the nanomachine to various concentrations of streptavidin.
Figure 16:
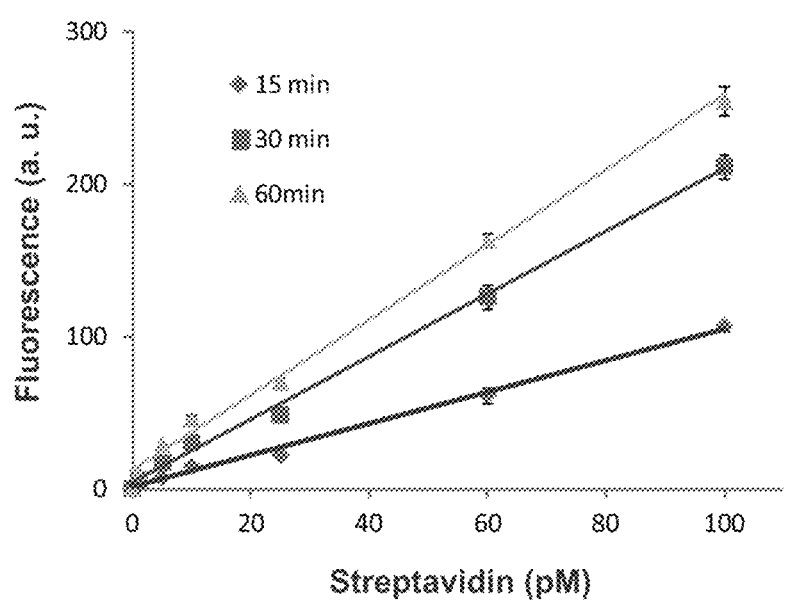
FIG. 16 is a graph depicting the overall fluorescence intensity as a function of streptavidin concentration.
Figure 17A:
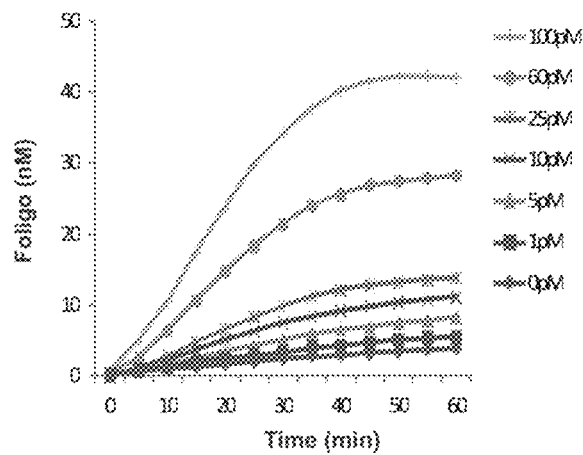
FIG. 17A Amounts of total Foligo generated by the nanomachine in response to varying concentrations of streptavidin.
Figure 17B:
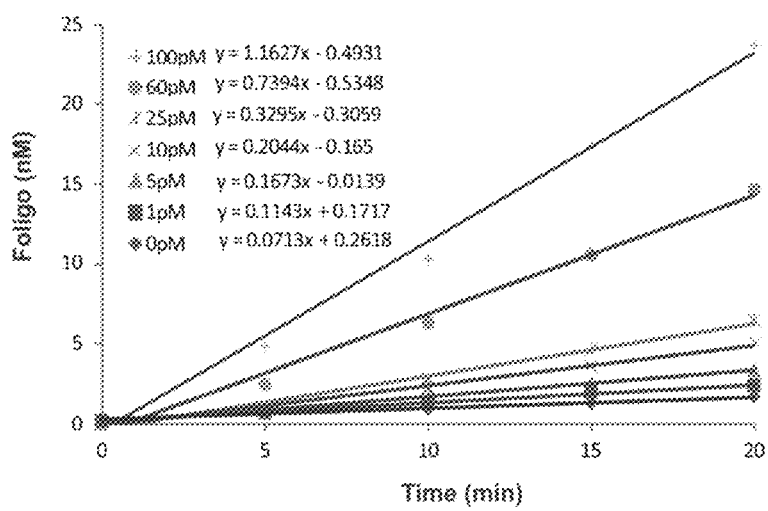
FIG. 17B Calculation of initial rates using data of the first 20 min of the nanomachine operation.
Figure 17C:
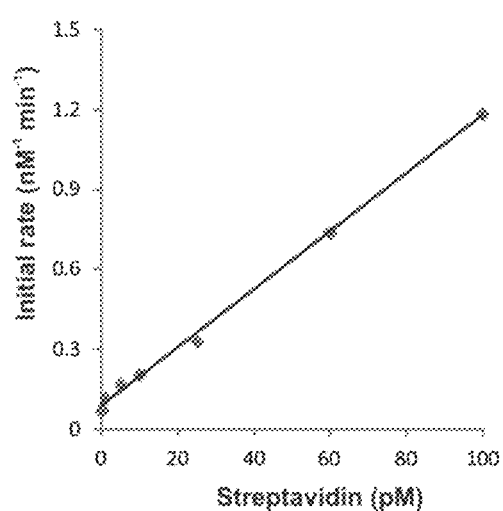
FIG. 17C The initial rate is proportional to the concentration of streptavidin.

Having observed that each active nanomachine operates with a similar progress profile, we reasoned that the total free Foligo in solution is the sum of Foligo cleaved from individual nanomachines and therefore is proportional to the streptavidin concentration. To test this, we measured progress curves resulting from various concentrations of streptavidin (FIG. 15). As expected, the overall fluorescence is proportional to the concentration of streptavidin. The fluorescence intensity at three representative time points is linearly related to the concentration of streptavidin (FIG. 16). The initial rate is also proportional to the streptavidin concentration (FIG. 17A, 17B, 17C). The nanomachine is able to differentiate 0.5 pM streptavidin from the blank. Therefore the nanomachine can be used for sensitive detection of biomolecules, which is conducted in homogeneous solutions, without the need for separation.

Figure 19A:
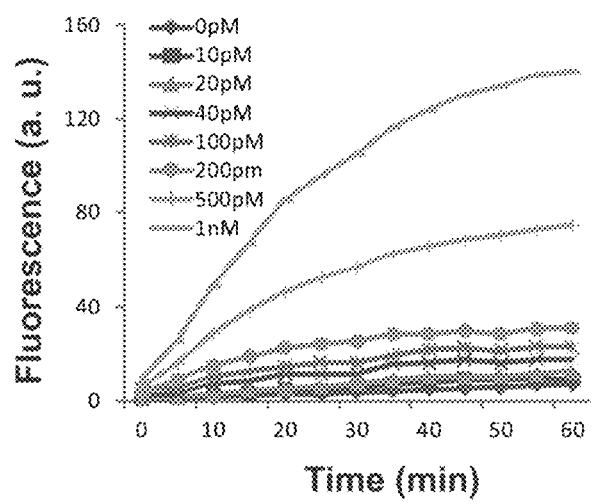
FIG. 19A Progress curves of the nanomachine in response to varying concentrations of PDGF-BB in cell lysate.

We further demonstrate that a simple alteration of affinity ligands enables the nanomachine to be responsive to any other biomolecules that can bind simultaneously to two ligands. As an example, we first used aptamers as affinity ligands to construct a nanomachine specifically responding to PDGF-BB. Because PDGF-BB is a homodimer, containing two identical B chains, we use one aptamer to act as both ligands L1 and L2. The binding of PDGF-BB to both aptamers, one on the AuNP and the second on the swing arm, turns on the nanomachine operation, initiating autonomous and iterative cleavage of the anchorage (FIG. 18A). A linear relationship was obtained between PDGF-BB concentration and fluorescence of the cleaved Foligo (FIG. 18B). PDGF-BB at 5 pM resulted in a fluorescence increase significantly different from background. We further examined the specificity of the nanomachine by measuring its response to five other proteins [human serum albumin (HSA), human immunoglobulin (IgG), lysozyme, prothrombin, and thrombin]. These five proteins at 10 nM concentration did not generate fluorescence distinguishable from the blank, whereas 1 nM PDGF-BB resulted in a large fluorescence increase (FIG. 18C). These results suggest that our nanomachine is specifically responsive to the target. The high specificity of the nanomachine largely arises from its distinct feature that activation of the nanomachine necessitates the simultaneous binding of two ligand molecules to the same target molecule. Similar progress curves were obtained when PDGF-BB was present in the cell lysate, further proving the specificity of the nanomachine (FIG. 19A, B).

We further demonstrated the use of DNA probes as affinity ligands to construct a nanomachine specifically responding to a DNA target. We used two DNA probes that enable sandwich hybridization with the Smallpox gene. We conjugated one of these probes to the AuNP and incorporated the other probe into the swing arm. The hybridization of a target sequence with two DNA probes brings the swing arm onto the AuNP surface, thereby activating the nanomachine and initiating the generation of Foligos (FIG. 20A). The nanomachine operates as expected with a linear relationship between target concentration and fluorescence intensity (FIG. 20B). The nanomachine is able to differentiate the fully matched target from a variant of single-mismatch (FIG. 20C). The construction of the nanomachine specifically responsive to a DNA target further demonstrates the applicability of nanomachines to various biomolecules.

Distinct from other DNA nanomachines that all rely on DNA self-assembly, the new nanomachines have several advantageous features. (i) The binding-induced DNA nanomachines harnesses specific target binding to trigger assembly of separate DNA components that are otherwise unable to spontaneously assemble. This strategy provides the opportunity to initiate a nanomachine by any target molecule that binds simultaneously to two ligands. (ii) This nanomachine achieves high density, three-dimensional DNA tracks on AuNPs. Other DNA nanomachines are mostly one- or two-dimensional. (iii) The operation of the nanomachine, powered by enzymatic cleavage of conjugated oligonucleotides, generates hundreds of oligonudeotides in response to a single binding event, enhancing the sensitivity. The concept and strategy have potential to further expand the dynamic DNA nanotechnology to proteins for diverse applications, e.g., regulating cell functions, delivering therapeutic drugs, and enhancing molecular imaging.

Citations

[1] P. Karagiannis, Y. Ishii, T. Yanagida, *Chem. Rev.* 2014, 114, 3318-3334.
[2] a) P. Yin, H. Yan, X. G. Daniell, A. J. Turberfield, J. H. Reif, *Angew. Chem. Int. Ed.* 2004, 43, 4906-4911; b) R. A. Muscat, J. Bath, A. J. Turberfield, *Small* 2012, 8, 3593-3597; c) Y. Tian, Y. He, Y. Chen, P. Yin, C. Mao, *Angew. Chem. Int. Ed.* 2005, 44, 4355-4358.
[3] a) B. Yurke, A. J. Turberfield, A. P. Mills, F. C. Simmel, J. L. Nemann, *Nature* 2000, 406, 605-608; b) M. Liu, J. Fu, C. Hejesen, Y. Yang, N. W. Woodbury, K. Gothelf, Y. Liu, H. Yan, *Nat. Commun.* 2013, 4, 2127; c) C. Zhou, Z. Yang, D. Liu, *J. Am. Chem. Soc.* 2012, 134, 1416-1418.
[4] a) T. G. Cha, J. Pan, H. Chen, J. Salgado, X. Li, C. Mao, J. H. Choi, *Nat. Nanotechnol.* 2014, 9, 39-43; b) S. Venkataraman, R. M. Dirks, P. W. Rothemund, E. Winfree, N. A. Pierce, *Nat. Nanotechnol.* 2007, 2, 490-494; c) M. Liber, T. E. Tomov, R. Tsukanov, Y. Berger, E. Nir, *Small* 2015, 11, 568-575.
[5] a) Y. Amir, E. Ben-Ishay, D. Levner, S. Ittah, A. Abu-Horowitz, I. Bachelet, *Nat. Nanotechnol.* 2014, 9, 353-357; b) K. Lund, et al. *Nature* 2010, 465, 206-210.
[6] a) J. M. Thomas, H. Z. Yu, D. Sen, *J. Am. Chem. Soc.* 2012. 134, 13738-13748; b) Y. Yang, G. Liu, H. Liu, D. Li, C. Fan, D. Liu, *Nano Lett.* 2010, 10, 1393-1397; c) F. Wang, X. Liu, I. Willner, *Angew. Chem. Int. Ed.* 2015, 54, 1098-1129.
[7] a) J. Bath, A. J. Turberfield, *Nat. Nanotechnol.* 2007, 2, 275-284; b) H. Liu, D. Liu, *Chem. Commun.* 2009, 21, 2625-2636.
[8] a) C. Song, Z. G. Wang, B. Ding, *Small* 2013, 22, 9, 2382-2392; b) Z. G. Wang, J. Elbaz, I. Willner, *Nano Lett.* 2011, 11, 304-309; c) A. Rajendran, M. Endo, K. Hidaka, H. Sugiyama, *J. Am. Chem. Soc.* 2013, 135, 1117-1123.
[9] S. M., Douglas, I. Bachelet, G. M. Church, *Science.* 2012, 335, 831-834.
[10] a) H. Zhang, X.-F. Li, X. C. Le, *Anal. Chem.* 2012, 84, 877-884; b) H. Zhang, F. Li, B. Dever, C. Wang, X.-F. Li, X. C. Le, *Angew. Chem. Int. Ed.* 2013, 52, 10698-10705; c) B. Deng, J. Chen, H. Zhang, *Anal. Chem.* 2014, 86, 7009-7016.
[11] a) B. Dubertret, M. Calame, A. J. Ubchaber, *Nat. Biotechnol.* 2001, 19, 365-370; b) B. Bhatt, P. J. Huang, N. Dave, J. Liu, *Langmuir* 2011, 27, 6132-6137; c) P. Wu, K. Hwang, T. Lan, Y. Lu, *J. Am. Chem. Soc.* 2013, 135, 5254-5257. d) U. Uddayasankar, U. J. Krull, *Anal. Chim. Acta.* 2013, 803, 113-122.
[12] a) J. J. Storhofff, R. Elghanian, C. A. Mirkin, R. L. Letsinger, *Langmuir* 2002, 18, 6666-6670; b) H. Kimura-Suda, D. Y. Petrovykh, M. J. Tarlov, L. J. Whitman, *J. Am. Chem. Soc.* 2003, 125, 9014-9015.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Binding-Induced DNA Nanomachines

1. Experimental Section

Materials and Reagents.

All DNA oligonucleotides were synthesized, labeled, and purified by Integrated DNA Technologies (IDT, Coralville, Iowa). The DNA sequences and modifications are listed in Table 1. A 20-nm gold nanoparticle solution was purchased from Ted Pella (Redding, Calif.). Nicking endonuclease, Nb.BbvCI, was obtained from New England BioLabs (Whitby, ON, Canada). PDGF-BB was obtained from R&D Systems (Minneapolis, Minn.). Streptavidin, BSA, HSA, human IgG, and lysozyme were obtained from Sigma-Aldrich (Oakville, ON, Canada). Prothrombin and thrombin were purchased from Haematologic Technologies Inc. (Essex Junction, Vt.). All other reagents were of analytical grade.

AuNP Functionalization.

The AuNPs were functionalized with an anchorage containing a 6-carboxyfluorescein (6-FAM) molecule at its 3'-end and a ligand-attached oligonucleotide (Streptavidin-L1, PDGF-L1, or Smallpox gene-L1 in Table 1) using a modified literature procedure.[1] Briefly, 30 µM anchorage was mixed with 30 µM ligand-attached oligonucleotide in 10 mM Tris-HCl (pH 7.4) at a molar ratio of 20:1. A measured aliquot of this mixture was added into 1 mL of 20-nm AuNP solution to make the molar ratio of total oligonucleotide to AuNP 1000:1. This solution was then incubated at room temperature overight. Fifty microliters of 1% Tween 20 was added to the solution to reduce adsorption and aggregation of AuNPs. Repeated steps consisting of addition of NaCl, sonication (20 s), and incubation (20 min) followed for eight times. In the first two cycles, 0.05 M NaCl was added each time. In the subsequent six cycles, 0.1 M NaCl was added in each repeated cycle. After each incremental addition of NaCl, the AuNP solution was sonicated for 20 s followed by incubation for 20 min at room temperature. After incubation at room temperature for another two days, the solution was centrifuged at 13,000 g for 20 min to separate the AuNPs from the unconjugated DNA. The AuNPs were washed four times using 1 mL of 10 mM Tris-HCl (pH 7.4) solution containing 0.05% Tween 20. The AuNPs were resuspended in 10 mM Tris-HCl (pH 7.4) solution to a final concentration of 2 nM, and stored at 4° C. prior to use.

Determination of Anchorage Loading on AuNPs.

To determine the anchorage loading amount per AuNP, we first released the conjugated anchorages from the AuNP surfaces using mercaptoethanol. After the anchorages were released into solution, the solution was centrifuged to precipitate AuNPs and the supematant containing the released anchorages was transferred into a new tube. The fluorescence of the anchorage solution was then measured and the anchorage loading amount was determined against a calibration. Specifically, 10 µL of 2 nM DNA-functionalized AuNP solution was mixed with 50 µL of 24 mM mercaptoethanol in 1×PBS. The mixture was then covered with foil and placed in the dark. After an overnight incubation at room temperature, 60 μL of 1×PBS was added. The solution was then centrifuged at 13,000 g for 20 min to precipitate AuNPs. A 100-μL supernatant was transferred into a 96-well plate (Fisher Scientific, Ottawa, ON), which was then loaded into a fluorescence microplate reader (Beckman Coulter, DTX 800) for fluorescence detection. Calibration consisted of a series of diluted solutions containing varying concentrations of anchorage (from 1 nM to 100 nM) in 1×PBS and 10 mM mercaptoethanol. The number of anchorage per-AuNP was then derived from the concentrations of AuNPs and anchorage.

Examination of the Binding-Induced DNA Nanomachine Performance.

To examine the performance of the binding-induced DNA nanomachine responding to streptavidin, we measured fluorescence from sample and blank solutions in real-time. Unless otherwise stated, sample solutions contained 100 pM streptavidin, 0.2 nM DNA-functionalized AuNP, 4 nM biotin-labeled swing arm, 100 nM Blocker-9 in 112 μL of 10 mM Tris-HCl (7.9) buffer containing 50 mM NaCl, 10 mM $MgCl_2$ and 0.02% BSA. Blank solutions contained all other components except streptavidin. These solutions were first incubated at room temperature for 20 min to allow binding of streptavidin to the biotin on the AuNP surface and the second biotin in the swing arm. In a separate tube, 2 μL of Nb.BbvCl corresponding to 20 units of the enzyme was mixed with 6 μL of 60 mM $H_2O_2$. This mixture was incubated at room temperature for 10 min to oxidize the DTT present in Nb.BbvCl storage buffer; otherwise the DTT could release anchorages from AuNPs, generating background fluorescence. This Nb.BbvCl mixture was then added to the above solution to make a total volume of 120 μL. One hundred and ten microliters of this solution was then transferred into a 96-well assay plate, which was then loaded onto the fluorescence microplate reader set at a temperature of 37° C. for real-time fluorescence detection. The fluorescence was measured every 5 min for a total of 1 h by using 485 nm for excitation and 515 nm for emission. A solution containing only 0.2 nM AuNPs was used to measure background fluorescence due to incomplete quenching and the effect of DTT on the release of anchorage.

The study of the performance of the nanomachine for PDGF-BB and Smallpox gene was similar to that for streptavidin. The different amounts of PDGF-BB or Smallpox gene were mixed with 0.2 nM functionalized AuNP, 4 nM swing arm of PDGF-BB or Smallpox gene, and 100 nM Blocker-9 in either 112 μL 10 mM Tris-HCl (7.9) solution or cell lysate (only for PDGF-BB). The 10 mM Tris-HCl (7.9) solution contained 50 mM NaCl, 10 mM $MgCl_2$ and 0.02% BSA. After incubation at room temperature for 30 min, 8 μL of hydrogen peroxide-treated Nb.BbVCl solution containing 20 units of enzyme was then added. Fluorescence was then measured in real-time every 5 min for a total of 1 h.

In the operation of the binding-induced DNA nanomachines, the movement of the swing arm DNA is not unidirectional, unlike other DNA walkers and motors. Existing DNA walkers and motor make use of DNA to build one or two dimensional DNA tracks with precise distances and positions. These were achieved by using DNA tracks that have anchor DNA strands. The use of anchorage-conjugated AuNPs as tracks cannot offer this same capability. However, our nanomachines have several unique and advantageous features over existing DNA walkers and motors. First, all existing DNA walkers and motors rely on DNA self-assembly and cannot be activated by proteins and other molecules, while our machines are applicable to any molecules capable of binding to two ligands. Second, existing DNA walkers and motors typically allow the movement of only several steps, fewer than 20 steps maximum[2, 3], while our nanomachines enable the movement of the swing arm with hundreds of steps in response to a single binding event. Third, we demonstrate for the first time the use of AuNPs as scaffold to build three-dimensional tracks, while other DNA tracks are one- or two-dimensional. The use of AuNPs also allows us to readily monitor the operation of the nanomachine in real-time by taking advantage of the excellent fluorescence quenching efficiency of AuNPs.

Cell Lysate Preparation.

Approximately 10 million human cells (CRL2522) in 1.0 mL medium were spun at 1,000 g for 5 min. The cell pellet was washed three times with 1.0 mL cold 1×PBS. The centrifugation was carried out at 1,000 g for 5 min for the first two washes, and at 4,000 g for 2 min for the last wash. The cell pellet was then resuspended in 1 mL cell lysate buffer containing 25 mM Tris-HCl (7.9), 50 mM NaCl, and 1% NP-40. After 20 min incubation at room temperature, the lysate was centrifuged at 4,000 g for 5 min. The supernatant was transferred to a new tube and stored at 4° C. until analysis.

TABLE 1

Summary of oligonucleotide sequences used in this study

| Oligonucleotides | Sequences (5' 3') |
|---|---|
| Anchorage-1 | HS-XXXXXXXXXXXXXXXGCTGAGGTTT-6-Carboxyfluorescein (6-FAM) (SEQ ID NO: 1) |
| Anchorage-2 | HS-XXXXXXXXXXXXXXGCTGAGGTT-6-FAM (SEQ ID NO: 2) |
| L1 for Streptavidin | HS-TTT TTT TTT TTT TTT TTT TTT TTT T-Biotin (SEQ ID NO: 3) |
| 40-nt swing arm | Biotin-XXXXXXXXXXXXCCTCAGC (SEQ ID NO: 4) |
| 60-nt swing arm | Biotin-XXXXXXXXXXXXXCCTCAGC (SEQ ID NO: 5) |
| 80-nt swing arm | Biotin-XXXXXXXXXXXXXXCCTCAGC (SEQ ID NO: 6) |
| Control DNA for celavage rate study | AAC CTC AGC ACG ACA ACA (SEQ ID NO: 7) |

TABLE 1-continued

Summary of oligonucleotide sequences used in this study

| Oligonucleotides | Sequences (5' 3') |
|---|---|
| L1 for PDGF-BB | HS-(T)$_{25}$[illegible aptamer sequence] (SEQ ID NO: 8) Aptamer sequence |
| Swing arm for PDGF-BB | [illegible]CCTCAGC (SEQ ID NO: 9) |
| Smallpox gene | TCA TGT GTA AGT TA C AGG ATC TAA TTG TGA (SEQ ID NO: 10) |
| Mismatched target | TCA TGT ATA AGT TA C AGG ATC TAA TTG TGA (SEQ ID NO: 11) |
| L1 for Smallpox gene | HS-(T)$_{25}$[illegible] (SEQ ID NO: 12) DNA Probe L1 sequence |
| Swing arm for Smallpox gene | [illegible]CTCAGC (SEQ ID NO: 13) DNA Probe L2 Sequence |
| Blocker-9 | GAGGACACG (SEQ ID NO: 14) |
| Blocker-10 | GAGGACACGA (SEQ ID NO: 15) |
| Blocker-11 | GAGGACACGAC (SEQ ID NO: 16) |
| Blocker-12 | GAGGACACGACA (SEQ ID NO: 17) |
| Spacing Oligo | HS-TTTTTTTTTT (SEQ ID NO: 18) |

TABLE 2

Summary of the effect of key parameters on the initial rate of the nanomachine

| Anchorages/AuNP | Initial rate (nM · min$^{-1}$) | Blocker[1] | Initial rate (nM · min$^{-1}$) | Anchorage[2] | Initial rate (nM · min$^{-1}$) |
|---|---|---|---|---|---|
| 385 | 1.21 ± 0.07 | Blocker-9 | 1.06 ± 0.03 | Anchorage-1 | 1.12 ± 0.04 |
| 242 | 0.83 ± 0.06 | Blocker-10 | 0.61 ± 0.05 | Anchorage-2 | 0.13 ± 0.02 |
| 222 | 0.77 ± 0.04 | Blocker-11 | 0.07 ± 0.01 | | |
| 114 | 0.58 ± 0.05 | Blocker-12 | 0.04 ± 0.01 | | |
| 70 | 0.23 ± 0.02 | | | | |

[1,2] Sequences of blocker and anchorage are shown in Table 1.

FIG. 2 depicts the design of the binding-induced DNA nanomachine. The binding-induced DNA nanomachine comprises a DNA-functionalized gold nanoparticle and a swing arm. Onto the surface of a single AuNP are conjugated hundreds of single-stranded anchorages and tens of an affinity ligand L1. Each anchorage is composed of a short sequence C1 that is attached onto the AuNP via a DNA spacer S1. A 6-carboxyfluorescein (FAM) molecule is labeled on the 3'-end of C1. The fluorescence of FAM is quenched by the single AuNP. The swing arm consists of a sequence C1* complementary to C1, and a poly-thymine spacer S2. The C1 and C1* are designed to contain only 7 nucleotides so that their hybrid is unstable at ambient temperature. A DNA blocker that competes with C1 in hybridization with C1* further minimizes target-independent hybridization. In the absence of target molecules, there is no interaction between the swing arm and the AuNP, and the nanomachine is inactive.

FIG. 3 depicts the operation of the binding-induced DNA nanomachine. A specific target binding brings the swing arm onto the AuNP surface, inducing the hybridization between C1* on the swing arm and C1 on the anchorage. C1* and C1 are designed in such a way that the C1*:C1 hybrid forms a nicking endonuclease (NEase) recognition sequence. NEase cleaves C1 from the hybrid, leaving single-stranded C1* available. The swing arm moves along the AuNP surface, bringing C1* to hybridize with C1 on the next anchorage. The iterative operation continues: movement of the swing arm along the AuNP surface, formation of the C1*:C1 hybrid, and enzymatic cleavage of C1 from the hybrid. Once C1 is cleaved, a fluorescently-labeled oligonucleotide (Foligo) is released from the AuNP, restoring quenched fluorescence. Thus, fluorescence generation serves as a surrogate for the monitoring of the nanomachine operation. The entire event is initiated by binding of a single target molecule to the two ligands (L1 and L2). The overall size of the loop after the binding-induced formation of the C1*:C1 hybrid can be estimated by counting the nucleotide number in the loop. The total number of nucleotides in the loop includes 40 nt (swing arm), 16 nt (S1 of anchorage) and 25 nt (poly T used to conjugate biotin to AuNP). Even without counting the size of streptavidin and two biotins, the loop (81 n.t.) s ~25 nm in length, larger than the AuNP diameter of 20 nm.

2. Characterization of DNA-Functionalized AuNP by Using TEM and UV-Vis Spectroscopy Because there are tens of ligands on each AuNP, it is important to avoid binding of the target to two AuNPs which could form large aggregation of AuNPs. The formation of large aggregation of AuNPs would affect the operation of the nanomachine. To examine whether there was large aggregation of AuNPs, we used TEM and UV-Vis absorption spectroscopy to characterize the nanomachine solutions that were prepared as described above in Experimental Section (Examination of the Binding-Induced DNA Nanomachine Performance). Four solutions contained 0.2 nM DNA-functionalized AuNP, 4 nM biotin-labeled swing arm, and 0, 25, 60, or 100 pM streptavidin in 10 mM Tris-HCl buffer (pH 7.9) containing 50 mM NaCl, 10 mM $MgCl_2$, and 0.02% BSA. The four solutions were incubated at room temperature for 20 min and then at 37° C. for one additional hour prior to analysis. TEM images of all four solutions containing 0, 25, 60, or 100 pM streptavidin showed no difference in particle size or shape (FIG. 5A). These results suggest that there is no AuNP aggregation under the operational conditions of the binding-induced DNA nanomachine. We further measured UV-Vis spectra of these four solutions. If AuNPs form aggregation, the solution color would change from red to purple and the UV-Vis absorption spectrum would shift to a longer wavelength. FIG. S2b shows no difference in UV-Vis absorption spectra of the four solutions. Therefore, both the TEM (FIG. 5A) and the UV-Vis spectral results (FIG. 5B) consistently show that there was no observable aggregation of AuNPs under our experimental conditions.

Two possible reasons could contribute to the desirable outcome of no AuNP aggregation: high negative charge density and steric hindrance, which result from high DNA density on AuNP surface and the presence of 4 nM biotin-labeled swing arm in the solution. High DNA surface density generates high negative charge density on AuNP surface and steric hindrance, which makes it slow to use DNA linkers or proteins to aggregate DNA-functionalized AuNPs. High concentration of $Na^+$ is often required to neutralize the negative charge and enhance the aggregation. For instance, Mirkin et al.[4] showed that overnight incubation at room temperature was needed to enable effective hybridization of a DNA target with two DNA-functionalized AuNPs. Chang et al.[5] showed that in the presence of 200 mM NaCl in the solutions, incubation for two hours was required to generate aggregation of AuNPs conjugated with about 42 aptamer strands using a protein target. In our study, a single AuNP was conjugated with about four hundred single-stranded DNA strands and the NaCl concentration was only 50 mM. Our DNA density was higher and the concentration of NaCl was lower, both unfavorable for forming aggregation. Therefore, the binding of the streptavidin to the first AuNP is fast, because DNA-functionalized AuNPs are favorable to protein association,[8] whereas the binding of a second AuNP to the streptavidin molecule can be very slow because of strong charge repulsion and steric hindrance. Compared to DNA-functionalized AuNPs, the biotin-labeled swing arm possesses much less charge repulsion and steric hindrance. The swing arm can therefore bind to the streptavidin molecule easier and faster than the second AuNP, which then further prevents AuNP aggregation.

FIG. 5A depicts TEM images of nanomachine solutions containing 0.2 nM DNA-functionalized AuNP, 4 nM biotin-labeled swing arm, and 0 (A), 25 (B), 60 (C) or 100 (D) pM streptavidin.

FIG. 5B depicts UV-visible absorption spectra of nanomachine solutions containing 0.2 nM DNA-functionalized AuNP, 4 nM biotin-labeled swing arm, and 0, 25, 60, or 100 pM streptavidin.

Figure 6:
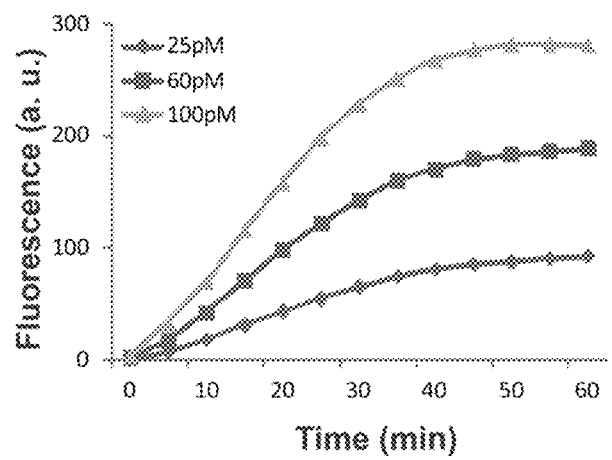
FIG. 6 depicts progress curves of the nanomachine in response to varying concentrations of streptavidin.
Figure 7:
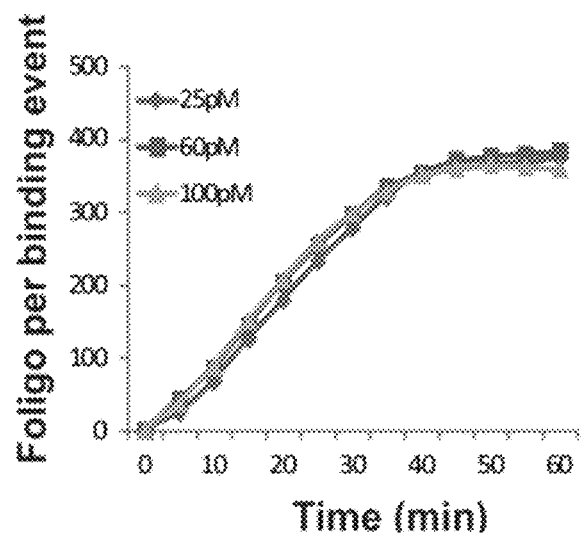
FIG. 7 is a graph depicting the number of Foligo generated from a single streptavidin molecule.

FIG. 6 depicts progress curves of the nanomachine in response to varying concentrations of streptavidin. To ensure that only a single streptavidin molecule is available to bind onto an AuNP, a limiting amount of streptavidin was incubated with an excess of AuNP. Three solutions were prepared to contain 200 pM AuNP and 100 pM, 60 pM, or 25 pM streptavidin. Therefore, in all three cases, only a single streptavidin molecule could be present on each activated nanomachine. The progress curves show the time-dependent increases in the overall fluorescence intensity. The overall fluorescence intensity is proportional to the total concentration of streptavidin (25, 60, and 100 pM) because a higher concentration of streptavidin in the solution activates more nanomachines, and therefore cleaves off more Foligo.

Figure 8:
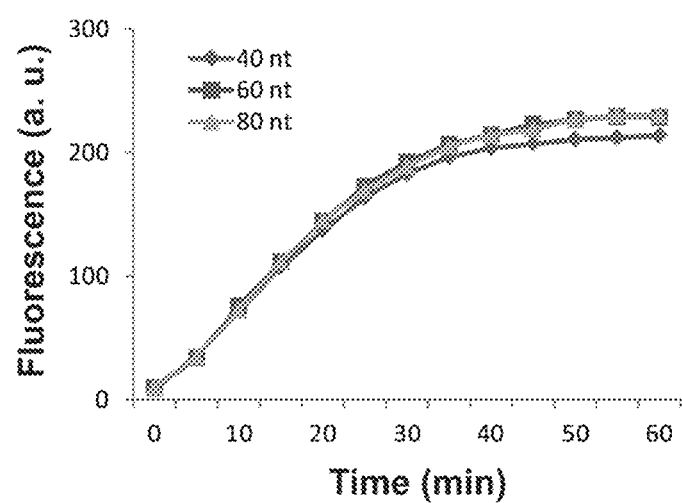
FIG. 8 depicts progress curves of three nanomachines that were constructed to have varying lengths of swing arms (40, 60, or 80 nucleotides in length)

FIG. 8 depicts progress curves of three nanomachines that were constructed to have varying lengths of swing arms (40, 60, or 80 nucleotides in length). Similar progress curves were obtained from the operation of these three nanomachines, indicating that these swing arms provide sufficient spatial distance to reach most anchorages on the AuNP. Each solution contained 200 pM AuNP and 100 pM streptavidin. nt denotes nucleotide.

Figure 9:
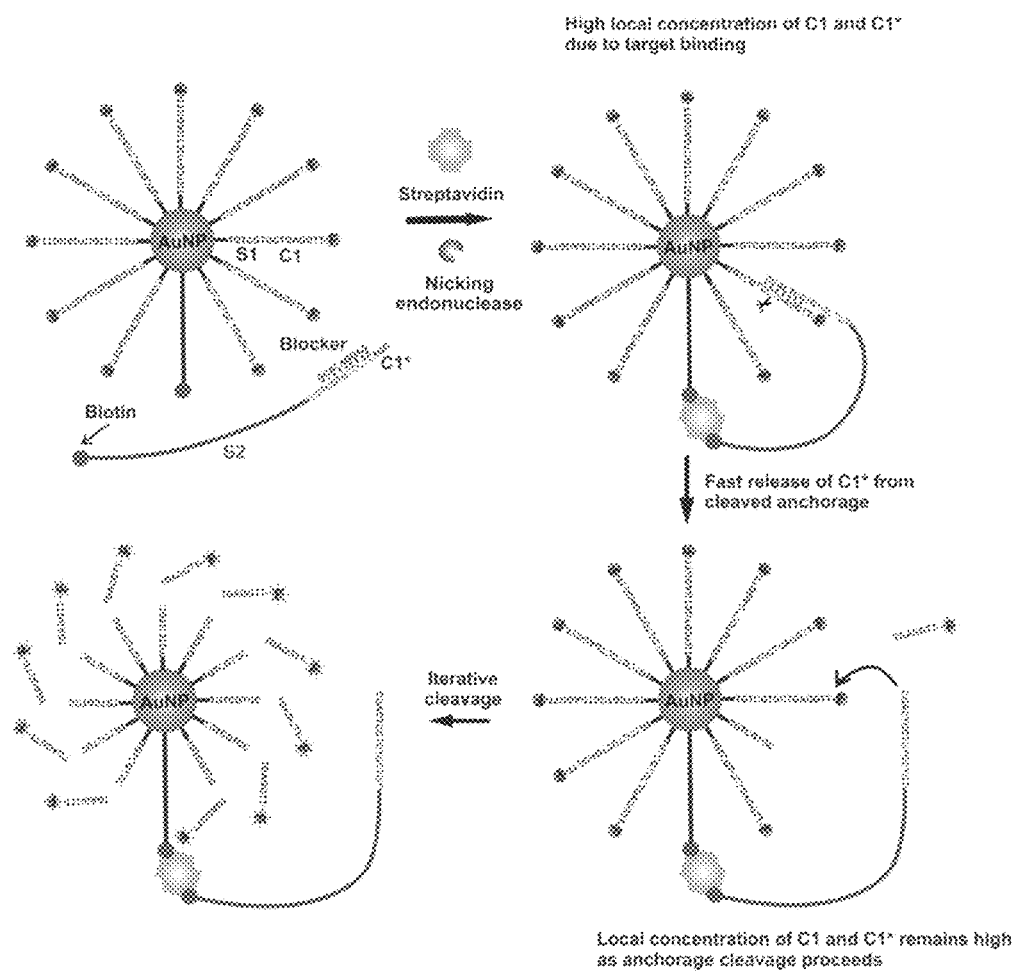
FIG. 9 depicts the enzymatic cleavage within the nanomachine occurs at a fast rate.

FIG. 9 depicts the enzymatic cleavage within the nanomachine occurs at a fast rate. The fast cleavage rate is due to two main reasons. First, the specific target binding places a single swing arm in close proximity to hundreds of anchorages on the AuNP surface and dramatically increases the local effective concentration of C1*, thereby facilitating the hybridization between C1* of the swing arm and C1 on different anchorages. Second, once C1 is enzymatically cleaved, the remaining portion of C1 on the anchorage has only two nucleotides, permitting the fast release of C1* from the anchorage.

FIG. 10 depicts hybridization by a control oligonucleotide containing 15 complementary bases and the subsequent endonuclease cleavage of the anchorage. Distinct from the swing arm which is not able to spontaneously hybridize with the anchorage, the control oligonucleotide is designed to spontaneously hybridize with the anchorage. This hybridization is an intermolecular association between two molecules: the oligonucleotide in solution and the anchorage on the AuNP. This is in contrast to the intramolecular hybridization between C1 and C1* within the nanomachine. In the case of the binding-induced nanomachine (FIG. 9), the initial binding event brings C1* to the same molecule as C1.

3. Modulation of the Capability of the Nanomachine to Generate Foligos Upon a Single Binding Event by Altering the Anchorage Loading Amount Per AuNP Because the number of Foligos generated from a single binding event is dependent on the number of anchorages available for hybridization with the swing arm, we studied the modulation of Foligo generation upon a single binding event by altering the anchorage loading amount. To prepare AuNPs conjugated with varying amounts of anchorage, we mixed the anchorage with a spacing oligo containing 10 thymine bases (Table 1) at different molar ratios. The mixtures of anchorage and spacing oligo were then incubated with AuNP solutions at the same molar ratio of total DNA to AuNPs. Therefore, similar amounts of total DNA were conjugated to AuNPs, whereas the anchorage loading amount decreased along with reducing the anchorage to the spacing oligo ratio because the spacing oligo competes with the anchorage in attaching to AuNP. We prepared five AuNPs with varying anchorage loading amounts: 385, 242, 222, 114, and 70 anchorages per AuNP. We used these five AuNPs to construct nanomachines and determined the performance of these nanomachines in response to a single streptavidin molecule by incubating 200 pM AuNP with 100 pM streptavidin. FIG. 12B shows that the number of Foligos generated from a single streptavidin molecule is proportional to the anchorage loading amount per AuNP, which implies that we are able to manipulate the capability of the nanomachine to release oligonucleotides in response to a single binding event by altering the anchorage loading amount.

Studies have reported that polyvalent nucleic acid-functionalized AuNPs stabilize nucleic acids against degradation by nucleases.[6-8] All these studies used DNase I to examine the stability enhancement. Mirkin et al.[6, 7] concluded that such enhanced stability of surface nucleic acids is attributed to high local salt concentrations (e.g. $Na^+$ and $K^+$) resulting from high oligonucleotide surface density, because monovalent cations, including $Na^+$ and $K^+$, inhibit the activity of DNase I and related nucleases. To further confirm their conclusion, Mirkin et al. used turbo DNase, a nuclease engineered to be more tolerant of monovalent cations, to replace DNase I, and they observed largely increased degradation of AuNP surface DNA, having a comparable rate to free DNA.[6]

We chose the nicking endonuclease Nb.BbvCI to perform the DNA cleavage in the binding-induced DNA nanomachines because this enzyme is able to cleave high density DNA from AuNP surface in the presence of high salt concentrations. Indeed, the nicking endonuclease Nb.BbVCI requires 50 mM $Na^+$ or $K^+$ and 10 mM $Mg^{2+}$ for optimum activity and it can tolerate high salt concentrations. Additionally, enzyme association is more favorable for DNA-functionalized AuNPs than free DNA.[6] We also found that interaction between the anchorage and the AuNP surface reduces the initial rate of nanomachines. High anchorage density makes all anchorages stand up straight on AuNP surface, reducing the interaction between the anchorage and the AuNP surface and favoring anchorage cleavage. Therefore, our nanomachines exhibit fast cleavage of anchorages from the AuNP surface.

FIGS. 12A and 12B depict modulation of the nanomachine to generate Foligos upon a single binding event. The modulation was achieved by altering the loading amount of anchorage on each AuNP. (a) The number of Foligos cleaved off from the different nanomachines. The five nanomachines contained different numbers of anchorages on each AuNP (from 70 to 385 anchorages per AuNP). (b) The number of Foligos generated from a single binding event is proportional to the loading amount of anchorage per AuNP. Each solution contained 200 pM AuNP and 100 pM streptavidin.

4. Tuning of the Initial Rate of the Nanomachine by Using Blockers with Different Lengths The blocker was designed to be partially complementary to one segment of C1* and another segment of S2. Therefore, the blocker competes with the anchorage in hybridizing with the swing arm C1, minimizing target-independent hybridization between the anchorage and the arm. When the specific target binding brings the swing arm onto the AuNP surface, the stability of the hybrid of the anchorage and the swing arm is greatly enhanced, displacing the blocker from the swing arm and resulting in hybridization between the anchorage and the swing arm. This binding-induced formation of the C1:C1* hybrid through displacement of the blocker from the swing arm can be understood by estimating the melting temperature of the C1:C1* hybrid before and after target binding. In the absence of target molecules, the hybridization between C1 and C1* is an intermolecular interaction, and the melting temperature of their hybrid is estimated to be 21.8° C. (using the IDT OligoAnalyzer 3.1 software and the following input parameters: 100 nM DNA, 50 mM NaCl, and 10 mM $MgCl_2$). Upon target binding, hybridization between C1* and C1 becomes an intramolecular interaction. Although we did not accurately determine the melting temperature of the C1:C1* hybrid after target binding, we can approximately estimate it by using a hairpin structure with C1:C1* as the stem sequence and a loop containing a number of thymidines. The number of thymidines used in the estimation is based on the distance between C1 and C1* after target binding. Without including the size of the streptavidin molecule and the distance between the L1 oligonucleotide and the specific anchorage conjugation sites on AuNP surface, the total number of nucleotides in the loop is 94, when the 60-nt swing arm is used (FIG. 2). Thus, with a loop containing 94 thymidines and the stem of C1:C1* (7 bp), the estimated melting temperature is 49.8° C. Assuming that the streptavidin molecule and the distance between the L1 oligonucleotide and the specific anchorage conjugation sites account for 30 thymidines, the estimated melting temperature is 48.0° C. The above estimation of the melting temperature of C1:C1* hybrid is approximate, serving as guidance for design of blockers.

We designed four blockers containing 9, 10, 11, and 12 nucleotides (nt). The melting temperatures of their corresponding C1*:blocker duplexes are estimated to be 36.2, 40.9, 45.1, and 49.0° C., respectively. We then examined the impact of these blockers on the initial rate of the nanomachine (FIGS. 13A and 13B). As expected, the increase in blocker length reduced the initial rate of the nanomachine. We chose the 9-nt blocker because of the good initial rate of the nanomachine (FIGS. 13A and 13B). The melting temperature of this 9-nt blocker:C1* duplex (36.2° C.) was lower than the estimated melting temperature of the C1:C1* hybrid after target binding (>48° C.). Thus, it is not surprizing that the binding-induced formation of C1:C1* hybrid is able to displace the 9-nt blocker from the swing arm. If the 11-nt blocker was used, the displacement would be more difficult, because the melting temperature of the 11-nt blocker:C1* duplex (45.1° C.) is closer to the estimated melting temperature of the C1:C1* hybrid after target binding and is higher than the operating temperature (37° C.).

In summary, in the absence of target molecules, the hybridization between C1 and C1* is not stable, and the estimated melting temperature of the C1:C1* hybrid (7 bp) is 21.8° C. Upon target binding and formation of a "hairpin" structure, the hybridization between C1 and C1* within the same molecule is more stable, and the estimated melting temperature of the C1:C1* hybrid (7 bp stem and a longer loop) is greater than 48° C. The estimated melting temperature of the 9-nt blocker:C* duplex (9 bp) is 36.2° C. Therefore, target binding can largely enhance the stability of the C1:C1* hybrid, enabling the displacement of the blocker from the swing arm and forming a stable C1:C1* hybrid.

FIGS. 13 and 13B shows reduction of the initial rate of the nanomachine by increasing the blocker length. (a) Generation of Foligo from nanomachines containing blockers of varying lengths (9, 10, 11 or 12 nt). (b) Calculation of the initial rates using data of the first 20 min. The increase in blocker length reduces the initial rate of the nanomachine. The sequences of blockers are listed in Table 1, and 100 nM of each blocker was used.

5. Effect of the Spacer S1 Sequence on the Initial Rate of the Nanomachine

Recognizing that nucleotides have varying binding affinity to the AuNP surface (A>C≥G>T),[9,10] we reasoned that varying the S1 sequence of the anchorage could alter the interaction between the anchorage and the AuNP surface, thereby affecting hybridization of C1*:C1 and the initial rate of the nanomachine. We designed two anchorages (anchorage-1 and anchorage-2) to consist of different S1 sequences (Table 1). The first S1 has eleven thymine bases at its attached end, whereas the corresponding sequence of the second S2 contains six guanine and five thymine bases. We then prepared AuNPs by using these two anchorages and examined the initial rate of the nanomachines made with these two anchorages. Anchorage-1 resulted in a much larger initial rate than anchorage-2 (FIGS. 14A and 14B), which suggests that reducing the thymine content of S1 can increase the interaction between the anchorage and the AuNP surface and decrease the initial rate of the nanomachine.

Figure 14B:
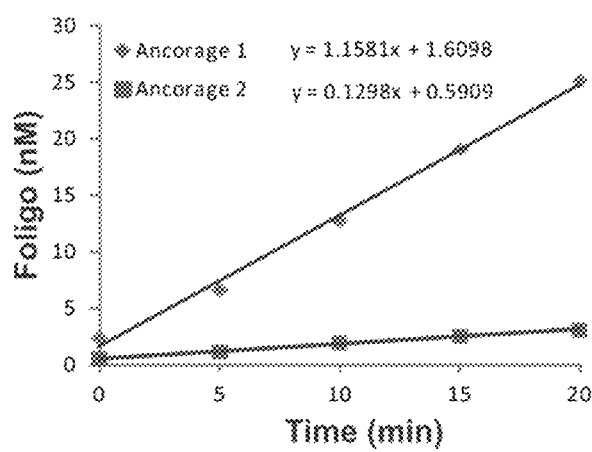
FIG. 14B Calculation of the initial rates using data of the first 20 min. Reducing the thymine content of S1 increases the interaction between the anchorage and the AuNP surface, thereby affecting the hybridization of the swing arm to the anchorage and decreasing the initial rate of the nanomachine.

FIGS. 14A and 148B depicts reduction of the initial rate of the nanomachine by reducing the thymine content of S1 on the anchorage. FIG. 14A Foligo generation curves using two anchorages with different S1 sequences. FIG. 14B Calculation of the initial rates using data of the first 20 min. Reducing the thymine content of S1 increases the interaction between the anchorage and the AuNP surface, thereby affecting the hybridization of the swing arm to the anchorage and decreasing the initial rate of the nanomachine. The sequences of two anchorages are listed in Table 1.

FIG. 16 depicts the overall fluorescence intensity as a function of streptavidin concentration. Data from 15 min, 30 min, and 60 min were plotted, representing the three phases of the nanomachine operation. A linear relationship was obtained between the fluorescence intensity and the concentration of streptavidin. A higher concentration of streptavidin activates more nanomachines, and produces correspondingly more Foligos. The overall fluorescence intensity is the sum of fluorescence from all Foligos that were cleaved off by each active nanomachine.

FIG. 17A, B depicts the initial rate is proportional to the concentration of streptavidin. FIG. 17A Amounts of total Foligo generated by the nanomachine in response to varying concentrations of streptavidin. FIG. 17B Calculation of initial rates using data of the first 20 min of the nanomachine operation. FIG. 17C The initial rate is proportional to the concentration of streptavidin.

Figure 19B:
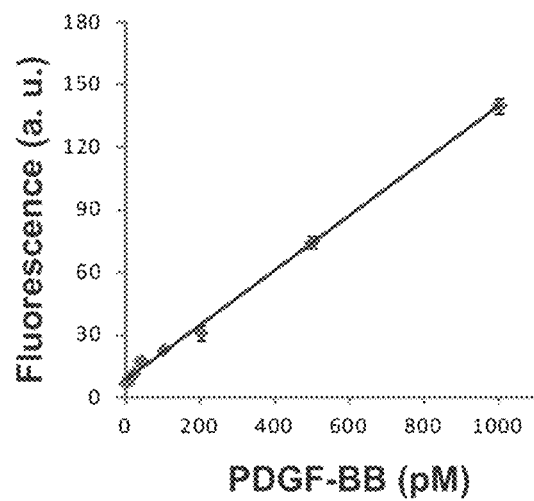
FIG. 19B The overall fluorescence intensity, corresponding to the amount of Foligo generated by the nanomachine, is proportional to the concentration of PDGF-BB.

FIG. 19 A, B. The specific response of the nanomachine to PDGF-BB spiked in cell lysate. FIG. 19A Progress curves of the nanomachine in response to varying concentrations of PDGF-BB in cell lysate. FIG. 19B The overall fluorescence intensity, corresponding to the amount of Foligo generated by the nanomachine, is proportional to the concentration of PDGF-BB.

Example 1 Citations

1. S. J. Hurst, A. K. Lytton-Jean, C. A. Mirkin, *Anal. Chem.* 2006, 78, 8313-8318.
2. S. F. Wckham, M. Endo, Y. Katsuda, K. Hidaka, J. Bath, H. Sugiyama, A. J. Turberfield. *Nat. Nanotechnol.* 2011, 6, 166-169.
3. J, Pan, F. Li, T. G. Cha, H. Chen, J. H. Choi. *Curr. Opin. Biotechnol.* 2015, 34, 56-64.
4. R. Elghanian, J. J. Storhoff, R. C. Mucic, R. L. Letsinger, C. A. Mirkin. *Science* 1997, 277, 1078-1081.
5. C. C. Huang, Y. F. Huang, Z. Cao, W. Tan, H. T. Chang. *Anal. Chem.* 2005, 77, 5735-5741.
6. D. S. Seferos, A. E. Prigodich, D. A. Giljohann, P. C. Patel, C. A. Mirkin. *Nano Lett.* 2009, 9, 308-311.
7. J. W. Zwanikken, P. Guo, C. A. Mirkin, M. O. de la Cruz. *J. Phys. Chem. C,* 2011, 115, 16368-16373.
8. N. Li, C. Chang, W. Pan, B. Tang. *Angew. Chem. Int. Ed.* 2012, 51, 7426-7430.
9. J. J. Storhofff, R. Elghanian, C. A. Mirkin, R. L. Letsinger, *Langmuir* 2002, 18, 6666-6670.
10. H. Kimura-Suda. D. Y. Petrovykh, M. J. Tarlov, L. J. Whitman, *J. Am. Chem. Soc.* 2003, 125, 9014-9015.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A nanomachine comprising:
a nanoparticle;
a first polynucleotide, the first polynucleotide having a first short sequence and a first spacer sequence, the first spacer sequence being conjugated to the nanoparticle and the first short sequence being conjugated to a first ligand;
a second polynucleotide, having a first end and a second end, the first end being conjugated to the nanoparticle and the second end being conjugated to a second ligand;
a third polynucleotide having a second short sequence, a second spacer sequence and a third ligand, the third ligand being conjugated to the second spacer sequence, the second short sequence being complementary to at least a portion of the first short sequence of the first polynucleotide;
a fourth polynucleotide that is complimentary to at least a portion of the second short sequence and the second spacer sequence of the third polynucleotide and being bound to the third polynucleotide; and
a target molecule that binds to the second ligand and the third ligand where, upon binding, the third polynucleotide is brought into proximity of the first polynucleotide such that the fourth polynucleotide is displaced and the first short sequence binds to the complimentary second short sequence, producing an enzymatic cleavage site, which is then cleaved by an enzyme and releasing the first ligand.

2. The nanomachine of claim 1 wherein the nanoparticle is a gold nanopartide.

3. The nanomachine of claim 1 wherein the enzymatic cleavage site is a nicking endonuclease site.

4. The nanomachine of claim 1 wherein the target molecule is a protein or nucleic acid.

5. The nanomachine of claim 4 wherein the protein is streptavidin.

6. The nanomachine of claim 4 wherein the protein is platelet derived growth factor.

7. The nanomachine of claim 5 wherein the second and third ligands are biotin.

8. The nanomachine of claim 6 wherein the second and third ligands are aptamers configured to bind to platelet derived growth factor.

9. The nanomachine of claim 1 wherein the second and third ligands, and the target molecule comprise a nucleic acid wherein the second and third ligands are complimentary to at least a portion of the target molecule.

10. The nanomachine of claim 1 wherein the first ligand is an effector molecule.

11. The nanomachine of claim 10 wherein the effector molecule is a labeling molecule, an affinity tag, a chemotherapeutic, a cytotoxic agent, an active peptide, a contrast agent, a radiolabel, DNA, or a small molecule inhibitor.

12. A method for effector molecule delivery comprising:
providing a functionalized nanoparticle having a first polynucleotide, the first polynucleotide having a first short sequence and a first spacer sequence, the first spacer sequence being conjugated to the nanoparticle and the first short sequence being conjugated to a first ligand; a second polynucleotide, having a first end and a second end, the first end being conjugated to the nanoparticle and the second end being conjugated to a second ligand; a third polynucleotide having a second short sequence, a second spacer sequence and a third ligand, the third ligand being conjugated to the second spacer sequence, the second short sequence being complementary to at least a portion of the first short sequence of the first polynucleotide; and a fourth polynucleotide that is complimentary to at least a portion of the second short sequence and the second spacer sequence of the third polynucleotide and being bound to the third polynucleotide;
adding a target molecule to the functionalized nanoparticle such that the target molecule binds to the second and third ligands, thereby bringing the third polynudeotide into proximity of the first polynucleotide such that the fourth polynucleotide is displaced and the first short sequence binds to the complimentary second short sequence, producing an enzymatic cleavage site;
enzymatically cleaving the first and third polynucleotides at the enzymatic cleavage site; and
releasing the first ligand, wherein the first ligand is the effector molecule.

13. The method of claim 12 wherein the nanoparticle is a gold nanoparticle.

14. The method of claim 12 wherein the enzymatic cleavage site is a nicking endonuclease site.

15. The method of claim 12 wherein the target molecule is a protein or nucleic acid.

16. The method of claim 15 wherein the protein is streptavidin and the second and third ligands are biotin.

17. The method of claim 15 wherein the protein is platelet derived growth factor and the second and third ligands are aptamers configured to bind to platelet derived growth factor.

18. The method of claim 12 wherein the second and third ligands, and the target molecule comprise a nucleic acid wherein the second and third ligands are complimentary to at least a portion of the target molecule.

19. The method of claim 12 wherein the effector molecule is a labeling molecule, an affinity tag, a chemotherapeutic, a cytotoxic agent, an active peptide, a contrast agent, a radiolabel, DNA, or a small molecule inhibitor.

* * * * *

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: Anchorage-1
<220> FEATURE:
<221> NAME/KEY: misc_feature
<222> LOCATION: (25)..(25)
<223> OTHER INFORMATION: 6-Carboxyfluorescein (6-FAM) attached to
      3'-end of oligonucleotide

<400> SEQUENCE: 1 ttttttttt tgtcgtgctg aggtt                                           25

<210> SEQ ID NO 2
<211> LENGTH: 25
<212> TYPE: DNA
<213> ORGANISM: Artificial Sequence
```

```
<220> FEATURE:
<223> OTHER INFORMATION: Anchorage-2
<220> FEATURE:
<221> NAME/KEY: misc_feature
<223> OTHER INFORMATION: 6-Carboxyfluorescein (6-FAM) attached to
      3'-end of oligonucleotide

<400> SEQUENCE: 2
ttggtgtggt gtgtttgctg aggtt                                              25

<210> SEQ ID NO 3
<211> LENGTH: 25
<212> TYPE: DNA
<213> ORGANISM: Artificial Sequence
<220> FEATURE:
<223> OTHER INFORMATION: L1 for Sterpavidin
<220> FEATURE:
<221> NAME/KEY: misc_feature
<223> OTHER INFORMATION: Biotin attached to 3'-end of oligonucleotide

<400> SEQUENCE: 3
tttttttttt tttttttttt ttttt                                              25

<210> SEQ ID NO 4
<211> LENGTH: 40
<212> TYPE: DNA
<213> ORGANISM: Artificial Sequence
<220> FEATURE:
<223> OTHER INFORMATION: 40 nt swing arm
<220> FEATURE:
<221> NAME/KEY: misc_feature
<223> OTHER INFORMATION: Biotin attached to 5'-end of oligonucleotide

<400> SEQUENCE: 4
tttttttttt tttttttttt tttttttgtcg tgtcctcagc                              40

<210> SEQ ID NO 5
<211> LENGTH: 60
<212> TYPE: DNA
<213> ORGANISM: Artificial Sequence
<220> FEATURE:
<223> OTHER INFORMATION: 60-nt swing arm
<220> FEATURE:
<221> NAME/KEY: misc_feature
<223> OTHER INFORMATION: Biotin attached to 5'-end of oligonucleotide

<400> SEQUENCE: 5
tttttttttt tttttttttt tttttttttt tttttttttt tttttttgtcg tgtcctcagc        60

<210> SEQ ID NO 6
<211> LENGTH: 80
<212> TYPE: DNA
<213> ORGANISM: Artificial Sequence
<220> FEATURE:
<223> OTHER INFORMATION: 80-nt swing arm
<220> FEATURE:
<221> NAME/KEY: misc_feature
<223> OTHER INFORMATION: Biotin attached to 5'-end of oligonucleotide

<400> SEQUENCE: 6
tttttttttt tttttttttt tttttttttt tttttttttt tttttttttt tttttttttt        60 tttttttgtcg tgtcctcagc                                                    80

<210> SEQ ID NO 7
<211> LENGTH: 15
<212> TYPE: DNA
<213> ORGANISM: Artificial Sequence
```

<220> FEATURE:
<223> OTHER INFORMATION: control DNA for cleavage rate study

<400> SEQUENCE: 7
aacctcagca cgaca                                                15

<210> SEQ ID NO 8
<211> LENGTH: 64
<212> TYPE: DNA
<213> ORGANISM: Artificial Sequence
<220> FEATURE:
<223> OTHER INFORMATION: L1 for PDGF-BB

<400> SEQUENCE: 8
tttttttttt tttttttttt tttttcacag gctacggcac gtagagcatc accatgatcc     60
tgtg                                                                  64

<210> SEQ ID NO 9
<211> LENGTH: 85
<212> TYPE: DNA
<213> ORGANISM: Artificial Sequence
<220> FEATURE:
<223> OTHER INFORMATION: Swing arm for PDGF-BB

<400> SEQUENCE: 9
cacaggctac ggcacgtaga gcatcaccat gatcctgtgt tttttttttt tttttttttt     60
tttttttttt tgtcgtgtcc tcagc                                           85

<210> SEQ ID NO 10
<211> LENGTH: 30
<212> TYPE: DNA
<213> ORGANISM: Artificial Sequence
<220> FEATURE:
<223> OTHER INFORMATION: Smallpox gene

<400> SEQUENCE: 10
tcatgtgtaa gttacaggat ctaattgtga                                      30

<210> SEQ ID NO 11
<211> LENGTH: 30
<212> TYPE: DNA
<213> ORGANISM: Artificial Sequence
<220> FEATURE:
<223> OTHER INFORMATION: Mismatched target

<400> SEQUENCE: 11
tcatgtataa gttacaggat ctaattgtga                                      30

<210> SEQ ID NO 12
<211> LENGTH: 40
<212> TYPE: DNA
<213> ORGANISM: Artificial Sequence
<220> FEATURE:
<223> OTHER INFORMATION: L1 for Smallpox gene

<400> SEQUENCE: 12
tttttttttt tttttttttt tttttcaca attagatcct                            40

<210> SEQ ID NO 13
<211> LENGTH: 31
<212> TYPE: DNA
<213> ORGANISM: Artificial Sequence
<220> FEATURE:
<223> OTHER INFORMATION: Swing arm for Smallpox gene

```
<400> SEQUENCE: 13
taacttacac atgatttgtc gtgtcctcag c                              31

<210> SEQ ID NO 14
<211> LENGTH: 9
<212> TYPE: DNA
<213> ORGANISM: Artificial Sequence
<220> FEATURE:
<223> OTHER INFORMATION: Blocker-9

<400> SEQUENCE: 14 gaggacacg                                                       9

<210> SEQ ID NO 15
<211> LENGTH: 10
<212> TYPE: DNA
<213> ORGANISM: Artificial Sequence
<220> FEATURE:
<223> OTHER INFORMATION: Blocker-10

<400> SEQUENCE: 15
gaggacacga                                                      10

<210> SEQ ID NO 16
<211> LENGTH: 11
<212> TYPE: DNA
<213> ORGANISM: Artificial Sequence
<220> FEATURE:
<223> OTHER INFORMATION: Blocker-11

<400> SEQUENCE: 16
gaggacacga c                                                    11

<210> SEQ ID NO 17
<211> LENGTH: 12
<212> TYPE: DNA
<213> ORGANISM: Artificial Sequence
<220> FEATURE:
<223> OTHER INFORMATION: Block-12

<400> SEQUENCE: 17
gaggacacga ca                                                   12

<210> SEQ ID NO 18
<211> LENGTH: 10
<212> TYPE: DNA
<213> ORGANISM: Artificial Sequence
<220> FEATURE:
<223> OTHER INFORMATION: Spacing Oligo

<400> SEQUENCE: 18
tttttttttt                                                      10
```